(12) United States Patent
Thomas

(10) Patent No.: US 6,844,341 B2
(45) Date of Patent: Jan. 18, 2005

(54) PYRIMIDINE DERIVATIVES FOR INHIBITION OF CELL PROLIFERATION

(75) Inventor: Andrew Peter Thomas, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/467,886

(22) PCT Filed: Feb. 12, 2002

(86) PCT No.: PCT/GB02/00603

§ 371 (c)(1),
(2), (4) Date: Aug. 13, 2003

(87) PCT Pub. No.: WO02/066481

PCT Pub. Date: Aug. 29, 2002

(65) Prior Publication Data

US 2004/0097506 A1 May 20, 2004

(30) Foreign Application Priority Data

Feb. 17, 2001 (GB) .............................................. 0103926

(51) Int. Cl.[7] .................. C07D 487/04; A61K 31/5025

(52) U.S. Cl. .................. 514/248; 514/249; 514/259.1; 544/236; 544/281; 544/350

(58) Field of Search ................................ 544/236, 281, 544/350; 514/248, 249, 259.1

(56) References Cited

U.S. PATENT DOCUMENTS

| | | | |
|---|---|---|---|
| 4,983,608 A | 1/1991 | Effland et al. | 514/256 |
| 5,516,775 A | 5/1996 | Zimmermann et al. | 514/224.2 |
| 5,521,184 A | 5/1996 | Zimmermann | 514/252 |
| 5,610,303 A | 3/1997 | Kimura et al. | 544/326 |
| 5,739,143 A | 4/1998 | Adams et al. | 514/278 |
| 5,859,041 A | 1/1999 | Liverton et al. | 514/396 |
| 6,593,326 B1 | 7/2003 | Bradbury et al. | 514/235.8 |
| 6,632,820 B1 | 10/2003 | Breault et al. | 514/256 |
| 6,649,608 B2 | 11/2003 | Pease et al. | 514/227.8 |
| 6,670,368 B1 | 12/2003 | Breault | 514/269 |

FOREIGN PATENT DOCUMENTS

| | | |
|---|---|---|
| CA | 2231765 | 9/1998 |
| EP | 0 135 472 | 3/1985 |
| EP | 0 363 002 | 4/1990 |
| EP | 0 379 806 B1 | 8/1990 |
| EP | 0 945 443 A1 | 9/1999 |
| WO | 91/18887 | 12/1991 |
| WO | 92/20642 | 11/1992 |
| WO | 95/09847 | 4/1995 |
| WO | 95/09851 | 4/1995 |
| WO | 95/09852 | 4/1995 |
| WO | 95/09853 | 4/1995 |

(List continued on next page.)

OTHER PUBLICATIONS

Volin et al., Cell Cycle Implications in the Pathogenesis of Rheumatoid Arthritis, Frontiers in Bioscience 5, d594–601, Jun. 2000.*
Blain et al., Differential Interaction of the Cyclin–dependent Kinase (CDK) Inhibitor p27Kip 1 with Cyclin A–CDK2 and Cyclin D2–CDK4, The J. of Biol. Chem., vol. 272, No. 41, pp. 25863–25872, Oct. 1997.*
Simone, Oncology: Introduction, Cecil Textbook of Medicine, 20th Edition, vol. 1, pp. 1004–1010, 1996.*
Boschelli et al., Synthesis and Tyrosine Kinase Inhibitory Activity of a Series of 2–Amino–8–H–pyrido[2,3–d]pyrimidines: Identifidation of Potent, Selective Platelet–Derived Growth Factor Receptor Tyrosine Kinase Inhibitors, J. Med. Chem., vol. 41, 1998, pp. 4365–4377.
Deady et al., "Reactions of some Quinazoline Compounds with Ethoxymethylenemalonic Acid Derivatives", J. Heterocyclic Chem., vol. 26, 1989, pp. 161–168.
El–Kerdawy et al.; "2,4–Bis (Substituted)–5–Nitropyrimidines of Expected Diuretic Action"; Egypt J. Chem. vol. 29, No. 2, 1986, pp. 247–251.
Fiziol Akt Veshchestva, 1975, vol. 7, pp. 68–72.
Ghosh et al.; "2,4–Bis(arylamino)–5–methylpyrimidines as Antimicrobial Agents"; J. Med. Chem., 1967, vol. 10, No. 5, pp. 974–975.
Ghosh, "2,4–Bis(arylamino)–6–methylpyrimidines as an antimicrobial agents", Chemical Abstract No. 97712f, vol. 95, 1981, pp. 648.
Schmidt et al.; "A Convenient Synthesis of 2–substituted 4–Amino–5–pyrimidinecarbonitriles"; J. Heterocycle Chem., 1997, vol. 24, No. 5, pp. 1305–1307.
Zimmermann et al., Phenylamino–Pyrimidine (PAP) Derivatives: A New Class of Potent and Selective Inhibitors of Protein Kinase C (PKC), Arch. Pharm. Pharm. Med. Chem., vol. 329, 1996, pp. 371–376.

*Primary Examiner*—Deepak Rao
(74) *Attorney, Agent, or Firm*—Morgan, Lewis & Bockius LLP

(57) ABSTRACT

Compounds of the formula (I): wherein Ring A, $R^1$, $R^3$, $R^4$, p, q, and n are as defined within and a pharmaceutically acceptable salts and in vivo hydrolyzable esters are described. Also described are processes for their preparation and their use as medicaments, particularly medicaments for producing a cell cycle inhibitory (anti-cell-proliferation) effect in a warm-quest-blooded animal, such as man.

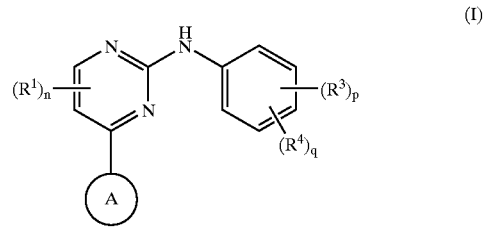

(I)

16 Claims, No Drawings

FOREIGN PATENT DOCUMENTS

| | | |
|---|---|---|
| WO | 96/15952 | 6/1995 |
| WO | 96/05177 | 2/1996 |
| WO | 96/28427 | 9/1996 |
| WO | 96/40143 | 12/1996 |
| WO | 97/19065 | 5/1997 |
| WO | 97/35856 | 10/1997 |
| WO | 97/40017 | 10/1997 |
| WO | 97/44326 | 11/1997 |
| WO | 97/47618 | 12/1997 |
| WO | 98/11095 | 3/1998 |
| WO | 98/16230 | 4/1998 |
| WO | 98/18782 | 5/1998 |
| WO | 98/25619 | 6/1998 |
| WO | 98/33798 | 8/1998 |
| WO | 98/41512 | 9/1998 |
| WO | 98/54093 | 12/1998 |
| WO | 98/56788 | 12/1998 |
| WO | 99/01136 | 1/1999 |
| WO | 99/32121 | 1/1999 |
| WO | 99/18096 | 4/1999 |
| WO | 99/18942 | 4/1999 |
| WO | 99/31073 | 6/1999 |
| WO | 99/41253 | 8/1999 |
| WO | 99/50250 | 10/1999 |
| WO | 99/50251 | 10/1999 |
| WO | 00/12485 | 3/2000 |
| WO | 00/12486 | 3/2000 |
| WO | 00/17202 | 3/2000 |
| WO | 00/17203 | 3/2000 |
| WO | 00/21926 | 4/2000 |
| WO | 00/25780 | 5/2000 |
| WO | 00/26209 | 5/2000 |
| WO | 00/39101 | 6/2000 |
| WO | 00/44750 | 8/2000 |
| WO | 00/49018 | 8/2000 |
| WO | 00/53592 | 9/2000 |
| WO | 00/55161 | 9/2000 |
| WO | 00/59892 | 10/2000 |
| WO | 00/78731 A1 | 12/2000 |
| WO | 01/14375 | 3/2001 |
| WO | 01/29009 A1 | 4/2001 |
| WO | 01/30778 A1 | 5/2001 |
| WO | 01/37835 A1 | 5/2001 |
| WO | 01/47897 A1 | 7/2001 |
| WO | 01/47921 A1 | 7/2001 |
| WO | 01/60816 A1 | 8/2001 |
| WO | 01/64653 A1 | 9/2001 |
| WO | 01/64654 A1 | 9/2001 |
| WO | 01/64655 A1 | 9/2001 |
| WO | 01/64656 A1 | 9/2001 |
| WO | 01/72717 A1 | 10/2001 |
| WO | 02/04429 A1 | 1/2002 |
| WO | 02/20512 A1 | 3/2002 |
| WO | 02/096887 A1 | 12/2002 |

* cited by examiner

PYRIMIDINE DERIVATIVES FOR INHIBITION OF CELL PROLIFERATION

The invention relates to pyrimidine derivatives, or pharmaceutically acceptable salts or in vivo hydrolysable esters thereof, which possess cell-cycle inhibitory activity and are accordingly useful for their anti-cell-proliferation (such as anti-cancer) activity and are therefore useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppressor gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

The present invention is based on the discovery that certain pyrimidine compounds surprisingly inhibit the effects of cell cycle kinases showing selectivity for CDK2, CDK4 and CDK6, and thus possess anti-cell-proliferation properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Accordingly, the present invention provides a compound of formula (I):

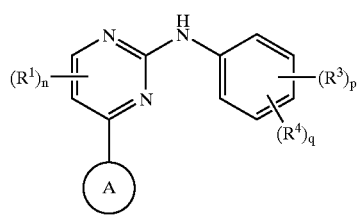

wherein:

Ring A is a group of formula (IA) or (IB):

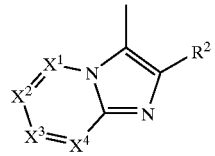

(IA)

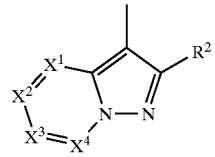

(IB)

wherein one or more of $X^1$, $X^2$, $X^3$ and $X^4$ are nitrogen and the others are $CR^5$ wherein the values of $R^5$ may be the same or different;

$R^1$ is halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, N-($C_{1-6}$alkyl)amino, N,N-($C_{1-6}$alkyl)$_2$amino, $C_{1-6}$akanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, N-($C_{1-6}$alkyl)sulphamoyl or N,N-($C_{1-6}$allyl)$_2$ sulphamoyl; wherein $R^1$ may be optionally substituted on carbon by one or more $R^6$;

$R^2$ and $R^5$ are independently of one other selected from hydrogen, halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl) carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl) sulphamoyl, N,N-($C_{1-6}$alkyl)$_2$sulphamoyl, phenyl, heterocyclic group, phenylthio or (heterocyclic group)thio; wherein any $R^2$ or $R^5$ may be optionally substituted on carbon by one or more $R^7$; and wherein if said heterocyclic group contains an —NH— moiety that nitrogen may be optionally substituted by a group selected from $R^8$;

n is 0 to 2, wherein the values of $R^1$ may be the same or different;

$R^3$ is halo, nitro, cyano, hydroxy, amino, carboxy, carbamoyl, mercapto, sulphamoyl, $C_{2-6}$alkenyl or $C_{2-6}$alkynyl;

p is 0–4; wherein the values of $R^3$ may be the same or different;

$R^4$ is a group A-E-; wherein

A is selected from $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$alkyl; wherein A may be optionally substituted on carbon by one or more $R^9$; and wherein if said heterocyclic group contains an —NH— moiety that nitrogen may be optionally substituted by a group selected from $R^{10}$;

E is a direct bond or —O—, —C(O)—, —OC(O)—, —C(O)O—, —N(R$^a$)C(O)—, —C(O)N(R$^a$)—, —N(R$^a$)—, —S(O)$_2$—, —SO$_2$N(R$^a$)— or —N(R$^a$)SO$_2$—; wherein R$^a$ is hydrogen or $C_{1-6}$alkyl optionally substituted by one or more $R^{11}$ and a is 0–2;

$R^9$ is independently selected from oxo, halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, C$_{1-6}$alkanoylamino, N-(C$_{1-6}$alkyl)carbamoyl, N,N-(C$_{1-6}$alkyl)$_2$carbamoyl, C$_{1-6}$alkylS(O)$_a$ wherein a is 0 to 2, C$_{1-6}$alkoxycarbonyl, C$_{1-6}$alkoxycarbonylamino, benzyloxycarbonylamino, N-(C$_{1-6}$alkyl)sulphamoyl and N,N-(C$_{1-6}$alkyl)$_2$sulphamoyl; wherein R$^9$ may be optionally substituted on carbon by one or more R$^{12}$;

q is 0–2; wherein the values of R$^4$ maybe the same or different; and wherein p+q≦5;

R$^6$, R$^7$, R$^{11}$ and R$^{12}$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-methylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and R$^8$ and R$^{10}$ are independently selected from C$_{1-4}$alkyl, C$_{1-4}$alkanoyl, C$_{1-4}$alkylsulphonyl, C$_{1-4}$alkoxycarbonyl, carbamoyl, N-(C$_{1-4}$alkyl)carbamoyl, N,N-(C$_{1-4}$alkyl) carbamoyl, benzyl, benzyloxycarbonyl, benzoyl and phenylsulphonyl;

or a pharmaceutically acceptable salt or an in vivo hydrolysable ester thereof.

In another aspect of the invention there is provided a compound of formula (I) as defined above, but wherein A is selected from C$_{1-6}$alkyl, phenyl, a heterocyclic group, C$_{3-8}$cycloalkyl, phenylC$_{1-6}$alkyl, (heterocyclic group)C$_{1-6}$ alkyl or C$_{3-8}$cycloalkylC$_{1-6}$cycloalkyl; wherein A may be optionally substituted on carbon by one or more R$^9$; and wherein if said heterocyclic group contains an —NH— moiety that nitrogen may be optionally substituted by a group selected from R$^{10}$.

In this specification the term "alkyl" includes both straight and branched chain alkyl groups but references to individual alkyl groups such as "propyl" are specific for the straight chain version only. For example, "C$_{1-6}$alkyl" includes C$_{1-4}$alkyl, C$_{1-3}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenylC$_{1-6}$alkyl" includes phenylC$_{1-4}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclic group" is a saturated, partially saturated or unsaturated, mono or bicyclic ring containing 4–12 atoms of which at least one atom is chosen from nitrogen, sulphur or oxygen, which may, unless otherwise specified, be carbon or nitrogen linked, wherein a —CH$_2$— group can optionally be replaced by a —C(O)— and a ring sulphur atom may be optionally oxidised to form the S-oxide(s). Examples and suitable values of the term "heterocyclic group" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, 4-pyridone, 1-isoquinolone, 2-pyrrolidone and 4-thiazolidone. Further examples and suitable values of the term "heterocyclic group" are morpholino, piperidyl, pyridyl, pyranyl, pyrrolyl pyrazolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl 3,5-dioxapiperidinyl, tetrahydropyranyl, imidazolyl, pyrimidyl, pyrazinyl, pyridazinyl, isoxazolyl, 4-pyridone, 1-isoquinolone, 2-pyrrolidone and 4-thiazolidone, particularly morpholino, pyrazolyl and pyrrolidinyl. Preferably a "heterocyclic group" is a saturated, partially saturated or unsaturated, mono or bicyclic ring containing 5 or 6 atoms of which at least one atom is chosen from nitrogen, sulphur or oxygen, it may, unless otherwise specified, be carbon or nitrogen linked, a —CH$_2$— group can optionally be replaced by a —C(O)— and a ring sulphur atom may be optionally oxidised to form the S-oxides.

An example of "C$_{1-6}$alkanoyloxy" is acetoxy. Examples of "C$_{1-6}$alkoxycarbonyl" include methoxycarbonyl, ethoxycarbonyl, n- and t-butoxycarbonyl. Examples of "C$_{1-6}$ alkoxy" include methoxy, ethoxy and propoxy. Examples of "C$_{1-6}$alkanoylamino" include formamido, acetamido and propionylamino. Examples of "C$_{1-6}$alkylS (O)$_a$ wherein a is 0 to 2" include methylthio, ethylthio, methylsulphinyl, ethylsulphinyl, mesyl and ethylsulphonyl. Examples of "C$_{1-6}$alkanoyl" include propionyl and acetyl. Examples of "N-(C$_{1-6}$alkyl)amino" include methylamino and ethylamino. Examples of "N,N-(C$_{1-6}$alkyl)$_2$amino" include di-N-methylamino, di-(N-ethyl)amino and N-ethyl-N-methylamino. Examples of "C$_{2-6}$alkenyl" are vinyl, alkyl and 1-propenyl. Examples of "C$_{2-6}$alkynyl" are ethynyl, 1-propynyl and 2-propynyl. Examples of "N-(C$_{1-6}$alkyl) sulphamoyl" are N-(methyl)sulphamoyl and N-(ethyl) sulphamoyl. Examples of "N-(C$_{1-6}$alkyl)$_2$sulphamoyl" are N,N-(dimethyl)sulphamoyl and N-(methyl)-N-(ethyl) sulphamoyl. Examples of "N-(C$_{1-6}$alkyl)carbamoyl" are methylaminocarbonyl and ethylaminocarbonyl. Examples of "N,N-(C$_{1-6}$alkyl)$_2$carbamoyl" are dimethylaminocarbonyl and methylethylaminocarbonyl. Examples of "C$_{3-8}$ cycloalkyl" are cyclopropyl, cyclobutyl, cyclopropyl and cyclohexyl. Examples of "(heterocyclic group)C$_{1-6}$alkyl" include pyridylmethyl 3-morpholinopropyl and 2-pyrimid-2-ylethyl. Examples of "(heterocyclic group)thio" include pyridylthio, 3-morpholinothio and 2-pyrimid-2-ylthio. Examples of "C$_{3-8}$cycloalkylC$_{1-6}$alkyl" are cyclopropylethyl, cyclobutylmethyl, 2-cyclopropylpropyl and cyclohexylethyl. Examples of "phenylC$_{1-6}$alkyl" are phenethyl, benzyl and 2-phenylpropyl.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$-alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

Some compounds of the formula (I) may have chiral centres and/or geometric isomeric centres (E- and Z-isomers), and it is to be understood that the invention encompasses all such optical, diastereoisomers and geometric isomers that possess CDK inhibitory activity.

The invention relates to any and all tautomeric forms of the compounds of the formula (I) that possess CDK inhibitory activity. In particular the skilled reader will appreciate that when $R^4$ is hydrogen, the imidazole ring as drawn in formula (I) may tautomerise.

It is also to be understood that certain compounds of the formula (I) can exist in solvated as well as unsolvated forms such as, for example, hydrated forms. It is to be understood that the invention encompasses all such solvated forms which possess CDK inhibitory activity.

Preferred values for the variable groups are as follows. Such values may be used where appropriate with any of the definitions, claims or embodiments defined hereinbefore or hereinafter.

In one aspect of the invention, preferably Ring A is a group of formula (IA).

In a further aspect of the invention, preferably Ring A is a group of formula (IB).

Preferably one of $X^1$, $X^2$, $X^3$ and $X^4$ are nitrogen and the others are $CR^5$ wherein the values of $R^5$ may be the same or different.

In one aspect of the invention, preferably $X^1$ is nitrogen and the others are $CR^5$ wherein the values of $R^5$ may be the same or different.

In another aspect of the invention, preferably $X^2$ is nitrogen and the others are $CR^5$ wherein the values of $R^5$ may be the same or different.

In an additional aspect of the invention, preferably $X^3$ is nitrogen and the others are $CR^5$ wherein the values of $R^5$ may be the same or different.

In an additional further aspect of the invention, preferably $X^4$ is nitrogen and the others are $CR^5$ wherein the values of $R^5$ may be the same or different.

Preferably $R^1$ is halo or $C_{1-6}$alkylS(O)$_a$ wherein a is 0; wherein $R^1$ may be optionally substituted on carbon by one or more $R^6$; wherein $R^6$ is hydroxy.

More preferably $R^1$ is bromo or 2-hydroxyethylthio.

Particularly $R^1$ is bromo or 2-hydroxyethylthio and n is 0–1.

Preferably $R^2$ is hydrogen.

In another aspect of the invention, preferably $R^2$ is selected from hydrogen, $C_{1-6}$alkyl or N,N-($C_{1-6}$alkyl)$_2$amino.

In another aspect of the invention, more preferably $R^2$ is selected from hydrogen, methyl, ethyl or N,N-dimethylamino.

Preferably $R^5$ is hydrogen.

In another aspect of the invention, preferably $R^5$ is selected from hydrogen, $C_{1-6}$alkyl or $C_{1-6}$alkoxy; wherein $R^5$ may be optionally substituted on carbon by one or more $R^7$; wherein $R^7$ is selected from halo.

In another aspect of the invention, more preferably $R^5$ is selected from hydrogen, methyl, methoxy or 2,2,2-trifluoroethoxy.

In one aspect of the invention, preferably n is 2, wherein the values of $R^1$ may be the same or different.

In a further aspect of the invention, preferably n is 1.

In an additional aspect of the invention, preferably n is 0.

Preferably $R^3$ is sulphamoyl.

In another aspect of the invention, preferably $R^3$ is sulphamoyl or halo.

In another aspect of the invention, more preferably $R^3$ is sulphamoyl or fluoro.

Preferably p is 0 or 1.

Preferably $R^4$ is a group A-E-; wherein
A is selected from $C_{1-6}$alkyl; wherein A may be optionally substituted on carbon by one or more $R^9$;
E is —N(R$^a$)C(O)—, —S(O)$_a$—, —SO$_2$N(R$^a$)— or —N(R$^a$)SO$_2$—; wherein R$^a$ is hydrogen or $C_{1-6}$alkyl and a is 0–2;
$R^9$ is independently selected $C_{1-6}$alkoxy and N,N-($C_{1-6}$alkyl)$_2$amino.

More preferably $R^4$ is a group A-E-; wherein
A is selected from methyl, ethyl or propyl; wherein A may be optionally substituted on carbon by one or more $R^9$;
E is —S(O)$_a$— or —NHSO$_2$—;
$R^9$ is independently selected from methoxy and N,N-dimethylamino.

Particularly $R^4$ is N-(2-dimethylaminoethyl)sulphamoyl, N-(2-methoxyethyl)sulphamoyl, N-methylsulphamoyl or N-(3-dimethylaminopropyl)sulphamoyl.

In another aspect of the invention, preferably $R^4$ is a group A-E-; wherein
A is selected from $C_{1-6}$alkyl, $C_{3-8}$cycloalkyl, (heterocyclic group)$C_{1-6}$alkyl or $C_{3-8}$cycloalkyl$C_{1-6}$alkyl; wherein A may be optionally substituted on carbon by one or more $R^9$;
E is —N(R$^a$)SO$_2$—; wherein R$^a$ is hydrogen or $C_{1-6}$alkyl;
$R^9$ is independently selected from hydroxy, $C_{1-6}$alkyl, $C_{2-6}$alkenyl, $C_{2-6}$alkynyl, $C_{1-6}$alkoxy, N,N-($C_{1-6}$alkyl)$_2$amino or $C_{1-6}$alkylS(O)$_a$ wherein a is 0.

In another aspect of the invention, more preferably $R^4$ is a group A-E-; wherein
A is selected from methyl, ethyl, propyl, isopropyl, t-butyl, cyclopropyl, cyclobutyl, morpholinoethyl, pyrrolidin-1-ylethyl, pyrazol-1-ylethyl or cyclopropylmethyl; wherein A may be optionally substituted on carbon by one or more $R^9$;
E is —N(R$^a$)SO$_2$—; wherein R$^a$ is hydrogen or methyl;
$R^9$ is independently selected from hydroxy, methyl, ethenyl, ethynyl, methoxy, ethoxy, propoxy, N,N-dimethylamino or methylthio.

In another aspect of the invention, particularly $R^4$ is N-methylsulphamoyl, N-cyclopropylmethylsulphamoyl, N-ethylsulphamoyl, N-propylsulphamoyl, N-allylsulphamoyl, N-2-propynylsulphamoyl, N-cyclobutylsulphamoyl, N-t-butylsulphamoyl, N-cyclopropylsulphamoyl, N-(2-dimethylaminoethyl) sulphamoyl, N-(2-methoxyethyl)sulphamoyl, N-(2-pyrazol-1-ylethyl)sulphamoyl, N-methyl-N-(2-methoxyethyl) sulphamoyl, N-(1-cyclopropylethyl)sulphamoyl, N-(3-dimethylaminopropyl)sulphamoyl, N-(3-methoxypropyl) sulphamoyl, N-(3-hydroxy-2-hydroxymethylprop-2-yl) sulphamoyl, N-(1,3-dihydroxyprop-2-yl)sulphamoyl, N-(3-morpholino-2-methylprop-2-yl)sulphamoyl, N-(1,3-dimethoxyprop-2-yl)sulphamoyl, N-(1,3-diethoxyprop-2-yl)sulphamoyl, N-(1-methoxyprop-2-yl)sulphamoyl, N-(1-ethoxyprop-2-yl)sulphamoyl, N-(1-hydroxyprop-2-yl) sulphamoyl, N-(3-methylthio-2-methylprop-2-yl) sulphamoyl, N-(3-pyrrolidin-1-yl-2-methylprop-2-yl) sulphamoyl, N-(3-methoxy-2-methylprop-2-yl)sulphamoyl, N-(2-methoxy-2-methylpropyl)sulphamoyl, N-(1-propoxyprop-2-yl)sulphamoyl or N-(3-hydroxy-2-methylprop-2-yl)sulphamoyl.

Preferably q is 0 or 1.
Preferably p+q is 1 or 2.
More preferably p+q is 1.
Particularly p+q is 1 and the $R^3$ or $R^4$ group is in the para position of the anilino group.

In another aspect of the invention preferably p+q is 0, 1 or 2; wherein the values of $R^3$ may be the same or different and the values of $R^4$ may be the same or different.

Therefore in a further aspect of the invention, there is provided a compound of formula (I) (as depicted above) wherein:
Ring A is a group of formula (IA);
one of $X^1$, $X^2$, $X^3$ and $X^4$ are nitrogen and the others are CH;
n is 0;
$R^2$ is hydrogen;
$R^3$ is sulphamoyl;
p is 0 or 1;
$R^4$ is N-(2-dimethylaminoethyl)sulphamoyl, N-(2-methoxyethyl)sulphamoyl, N-methylsulphamoyl or N-(3-dimethylaminopropyl)sulphamoyl.
q is 0 or 1;
p+q is 1 and the $R^3$ or $R^4$ group is in the para position of the anilino group;
or a pharmaceutically acceptable salt or an in vivo hydrolysable ester thereof.

Therefore in another aspect of the invention, there is provided a compound of formula (I) (as depicted above) wherein:
Ring A is a group of formula (IA) (as depicted above)
wherein one of $X^1$, $X^2$, $X^3$ and $X^4$ is nitrogen and the others are $CR^5$; wherein the values of $R^5$ maybe the same or different;
n is 0;
$R^2$ is selected from hydrogen, $C_{1-6}$alkyl or N,N-($C_{1-6}$alkyl)$_2$amino;
$R^5$ is selected from hydrogen, $C_{1-6}$alkyl or $C_{1-6}$alkoxy; wherein $R^5$ may be optionally substituted on carbon by one or more $R^7$; wherein $R^7$ is selected from halo;
$R^3$ is sulphamoyl or halo;
p is 0 or 1;
$R^4$ is a group A-E-; wherein
A is selected from $C_{1-6}$alkyl, $C_{3-8}$cycloalkyl, (heterocyclic group)$C_{1-6}$alkyl or $C_{3-8}$cycloalkyl$C_{1-6}$alkyl; wherein A may be optionally substituted on carbon by one or more $R^9$;

E is —N($R^a$)SO$_2$—; wherein $R^a$ is hydrogen or $C_{1-6}$alkyl;
$R^9$ is independently selected from hydroxy, $C_{1-6}$alkyl, $C_{2-6}$alkenyl, $C_{2-6}$alkynyl, $C_{1-6}$alkoxy, N,N-($C_{1-6}$alkyl)$_2$ amino or $C_{1-6}$alkylS(O)$_a$ wherein a is 0;
q is 0 or 1;
p+q is 0, 1 or 2; wherein the values of $R^3$ maybe the same or different and the values of $R^4$ may be the same or different;
or a pharmaceutically acceptable salt or an iii vivo hydrolysable ester thereof.

Therefore in an additional aspect of the invention, there is provided a compound of formula (I) (as depicted above) wherein:
Ring A is a group of formula (IA) (as depicted above)
wherein one of $X^1$, $X^2$, $X^3$ and $X^4$ is nitrogen and the others are $CR^5$; wherein the values of $R^5$ may be the same or different;
n is 0;
$R^2$ is selected from hydrogen, methyl, ethyl or N,N-dimethylamino;
$R^5$ is selected from hydrogen, methyl, methoxy or 2,2,2-trifluoroethoxy;
$R^3$ is sulphamoyl or fluoro;
p is 0 or 1;
$R^4$ is N-methylsulphamoyl, N-cyclopropylmethylsulphamoyl, N-ethylsulphamoyl, N-propylsulphamoyl, N-allylsulphamoyl, N-2-propynylsulphamoyl, N-cyclobutylsulphamoyl, N-t-butylsulphamoyl, N-cyclopropylsulphamoyl, N-(2-dimethylaminoethyl)sulphamoyl, N-(2-methoxyethyl) sulphamoyl, N-(2-pyrazol-1-ylethyl)sulphamoyl, N-methyl-N-(2-methoxyethyl)sulphamoyl, N-(1-cyclopropylethyl) sulphamoyl, N-(3-dimethylaminopropyl)sulphamoyl, N-(3-methoxypropyl)sulphamoyl, N-(3-hydroxy-2-hydroxymethylprop-2-yl)sulphamoyl, N-(1,3-dihydroxyprop-2-yl)sulphamoyl, N-(3-morpholino-2-methylprop-2-yl)sulphamoyl, N-(1,3-dimethoxyprop-2-yl) sulphamoyl, N-(1,3-diethoxyprop-2-yl)sulphamoyl, N-(1-methoxyprop-2-yl)sulphamoyl, N-(1-ethoxyprop-2-yl) sulphamoyl, N-(1-hydroxyprop-2-yl)sulphamoyl, N-(3-methylthio-2-methylprop-2-yl)sulphamoyl, N-(3-pyrrolidin-1-yl-2-methylprop-2-yl)sulphamoyl, N-(3-methoxy-2-methylprop-2-yl)sulphamoyl, N-(2-methoxy-2-methylpropyl)sulphamoyl, N-(1-propoxyprop-2-yl) sulphamoyl or N-(3-hydroxy-2-methylprop-2-yl) sulphamoyl;
q is 0 or 1;
p+q is 0, 1 or 2; wherein the values of $R^3$ may be the same or different and the values of $R^4$ may be the same or different;
or a pharmaceutically acceptable salt or an in vivo hydrolysable ester thereof.

In another aspect of the invention, preferred compounds of the invention are any one of the Examples or a pharmaceutically acceptable salt or an in vivo hydrolysable ester thereof.

In another aspect of the invention, preferred compounds of the invention are any one of Examples 7, 27, 29, 39, 41, 42, 46, 63, 64 or 66 or a pharmaceutically acceptable salt or an in vivo hydrolysable ester thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt or an in vivo hydrolysable ester thereof which process (wherein variable groups are, unless otherwise specified, as defined in formula (I)) comprises of:

a) reaction of a pyrimidine of formula (II):

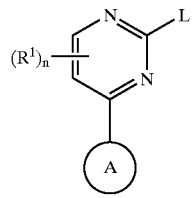

wherein L is a displaceable group; with an amine of formula (III):

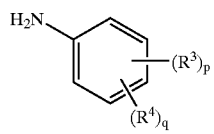

b) reacting a pyrimidine of formula (IV):

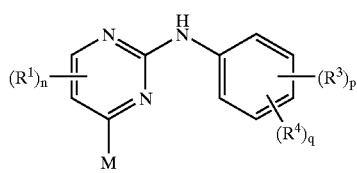

with a compound of the formula (V):

wherein one of M and Q is a displaceable group X and the other is an metallic reagent Y; or c) reacting a compounds of formula (VI):

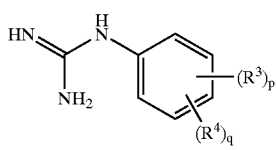

with a compound of formula (VII):

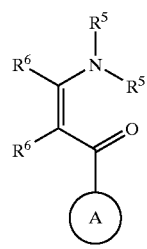

wherein $R^5$ is $C_{1-6}$alkyl and $R^6$ is hydrogen or $R^1$;

d) reacting an amino compound of formula (VIII):

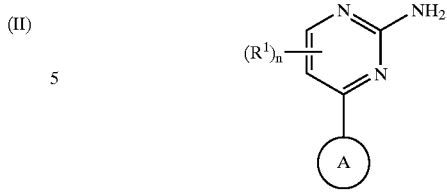

with a compound of formula (IX):

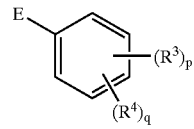

wherein E is a displaceable group; and thereafter if necessary.

i) converting a compound of the formula (I) into another compound of the formula (I);

ii) removing any protecting groups;

iii) forming a pharmaceutically acceptable salt or in vivo hydrolysable ester.

L is a displaceable group, suitable values for L are for example, a halogeno, methylthio or sulphonyloxy group, for example a chloro, bromo, methanesulphonyloxy or toluene-4-sulphonyloxy group.

E is a displaceable group, suitable values for E are for example, a halogeno or sulphonyloxy group, for example a chloro, bromo, iodo or trifluoromethanesulphonyloxy group.

A suitable displaceable group X is, for example, a halogeno or sulphonyl group, for example a bromo, iodo or trifluoromethylsulphonyl group.

A suitable metallic group Y, is, for example, copper, lithium, an organoboron reagent such as —$B(OH)_2$, —$B(OPr^i)_2$ or —$B(Et)_2$, or an organotin compound such as $SnBu_3$, an organosilicon compound such as $Si(Me)F_2$, an organozirconium compound such as $ZrCl_3$, an organoaluminium compound such as $AlEt_2$, an organomagnesium compound such as MgBr, an organozinc compound such as ZnCl or an organomercury compound such as HgBr.

Specific reaction conditions for the above reactions are as follows.

a) Pyrimidines of formula (II) and amines of formula (III) may be reacted together:

i) in the presence of a suitable solvent for example a ketone such as acetone or an alcohol such as ethanol or butanol or an aromatic hydrocarbon such as toluene or N-methyl pyrrolidine, optionally in the presence of a suitable acid for example an inorganic acid such as hydrochloric acid or sulphuric acid, or an organic acid such as acetic acid or formic acid (or a suitable Lewis acid) and at a temperature in the range of 0° C. to reflux, preferably reflux; or ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) may be prepared according to the following scheme:

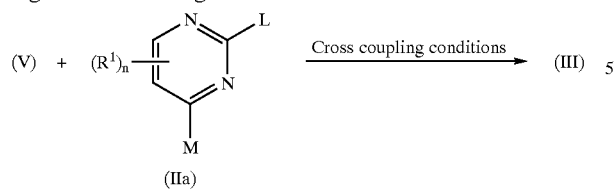

wherein one of M and Q is a displaceable group X as defined above and the other is an metallic reagent Y as defined above.

Cross coupling conditions are well known in the art Suitable conditions include, for example, those described under b) below.

Where Ring A is a group of formula (IA) and L is methylthio, compounds of the formula (II) may also be prepared according to the following scheme:

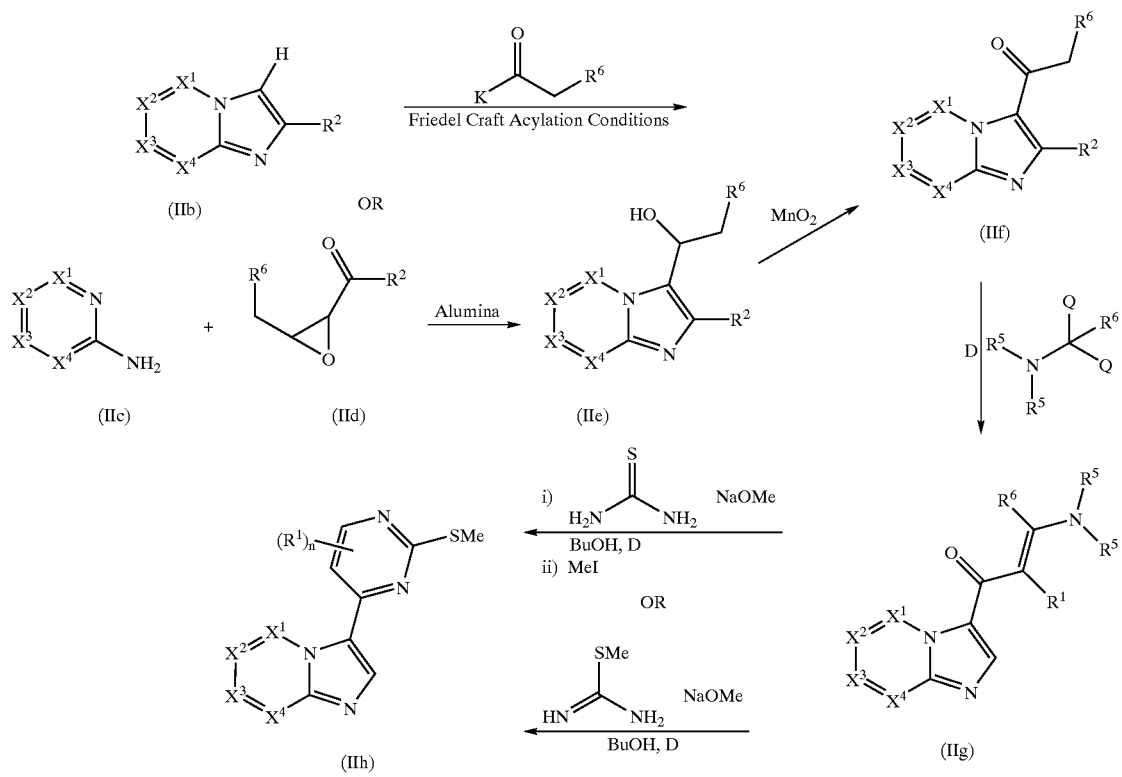

K is a suitable leaving group (for example $C_{1-6}$alkanoyloxy), $R^5$ and $R^6$ are as defined above, Q is a suitable leaving group (for example $C_{1-6}$alkoxy).

Where Ring A is a group of formula (IB) and L is methylthio, compounds of the formula (II) may also be prepared according to the following scheme:

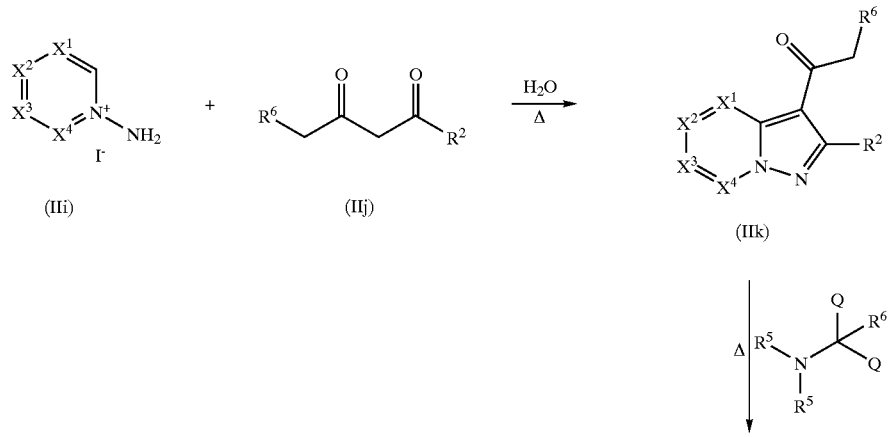

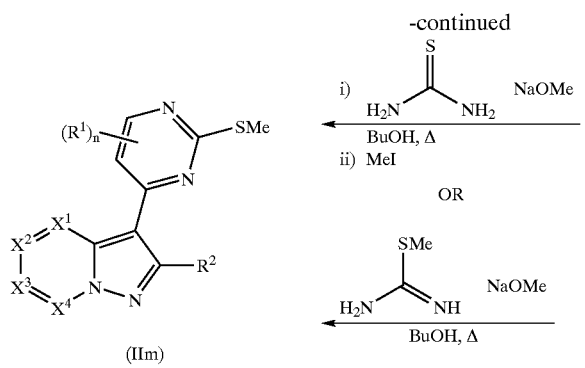

(IIm)

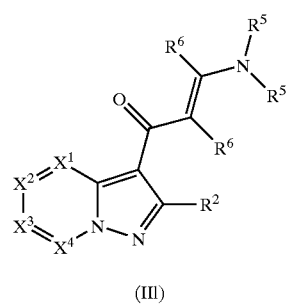

(III)

wherein R⁵ and R⁶ are as defined above.

Compounds of formula (IIg) or (III) may be further modified to produce compounds of formula (IIn):

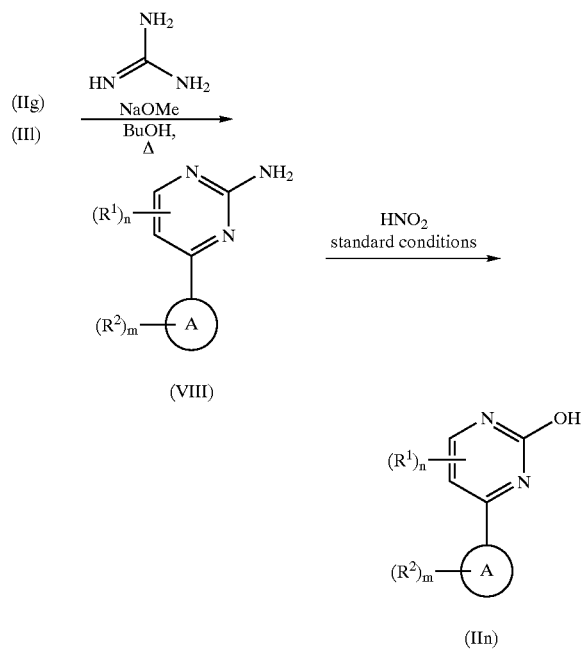

(IIn)

It will be appreciated by those skilled in the art that compounds of formula (IIn) may be additionally modified by standard functional group modification reactions known in the art to produce compounds of formula (II) where L is other leaving groups for example chloro, bromo, tosyl and mesyl.

Compounds of formula (IIa), (IIb), (IIc), (IId), (IIi) and (IIj) are commercially available compounds, or they are known in the literature, or they are prepared by standard processes known in the art.

b) Compounds of formula (IV) and compounds of formula (V) may be reacted together under standard cross coupling conditions. Examples of these are in the presence of a catalyst, for example, a metallic catalyst such as tetrakis(triphenylphosphine)palladium(0), palladium(II) chloride, palladium(II) bromide, nickel(II) chloride, nickel(II) bromide or bis(triphenylphosphine)nickel(II) chloride, in the presence of a suitable inert solvent or diluent, for example tetrahydrofuran, 1,4-dioxan, 1,2-dimethoxyethane, benzene, toluene, xylene, methanol or ethanol. The reaction is preferably conducted in the presence of a suitable base such as, for example, sodium carbonate or potassium carbonate, pyridine, 4-dimethylaminopyridine, triethylamine or morpholine, and conveniently at a temperature in the range, for example 10 to 250° C., preferably in the range 60 to 120° C.

Compounds of formula (IV) may be prepared according to the following scheme:

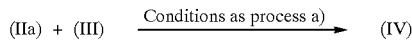

Compounds of formula (V) are commercially available compounds, or they are known in the literature, or they are prepared by standard processes known in the art.

c) compounds of formula (VI) and compounds of formula (VII) are reacted together in a suitable solvent such as N-methylpyrrolidinone or butanol at a temperature in the range of 100–200° C., preferably in the range of 150–170° C. The reaction is preferably conducted in the presence of a suitable base such as, for example, sodium methoxide or potassium carbonate.

Compounds of formula (VI) and (VII) are commercially available compounds, or they are known in the literature, or they are prepared by standard processes known in the art, or compounds of formula (VI) may be prepared by a process similar to that described for (IIf) and (IIk) hereinabove.

d) Amino compounds of formula (VI) and compounds of formula (IX) may be reacted together under standard Buchwald conditions such as those described under process a(ii) above.

Compounds of formula (VIII) are prepared as described above.

Compounds of formula (IX) are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possesses anti-cell-proliferation activity such as anti-cancer activity which is believed to arise from the CDK inhibitory activity of the compound. These properties may be assessed, for example, using the procedure set out below:-

Assay

The following abbreviations have been used:-

HEPES is N-[2-Hydroxyethyl]piperazine-N'-[2-ethanesulfonic acid)
DTT is Dithiothretiol
PMSF is Phenylmethylsulfonyl fluoride The compounds were tested in an in vitro kinase assay in 96 well format using Scintillation Proximity Assay (SPA—obtained from Amersham) for measuring incorporation of [γ-33-P]-Adenosine Triphosphate into a test substrate (GST-Retinoblastoma protein; GST-Rb). In each well was placed the compound to be tested (diluted in DMSO and water to correct concentrations) and in control wells either roscovitine as an inhibitor control or DMSO as a positive control.

Approximately 0.2 $\mu$l of CDK2/Cyclin E partially-purified enzyme (amount dependent on enzyme activity) diluted in 25 $\mu$l incubation buffer was added to each well then 20 $\mu$l of GST-Rb/ATP/ATP33 mixture (containing 0.5 $\mu$g GST-Rb and 0.2 $\mu$M ATP and 0.14 $\mu$Ci [γ-33-P]-Adenosine Triphosphate in incubation buffer), and the resulting mixture shaken gently, then incubated at room temperature for 60 minutes.

To each well was then added 150 $\mu$L stop solution containing (0.8 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124×g., for 5 minutes. The plates were read on a Topcount for 30 seconds per well.

The incubation buffer used to dilute the enzyme and substrate mixes contained 50 mM HEPES pH 7.5, 10 mM MnCl$_2$, 1 mM DTT, 100 $\mu$M Sodium vanadate, 100 $\mu$M NaF, 10 mM Sodium Glycerophosphate, BSA (1 mg/ml final).

Test Substrate

In this assay only part of the retinoblastoma protein (Science 1987 March 13;235(4794):1394–1399; Lee W. H., Bookstein R., Hong F., Young L. J., Shew J. Y., Lee E. Y.) was used, fused to a GST tag. PCR of retinoblastoma gene encoding amino acids 379–928 (obtained from retinoblastoma plasmid ATCC pLRbRNL) was performed, and the sequence cloned into pGEX 2T fusion vector (Smith D. B. and Johnson, K. S. Gene 67, 31 (1988); which contained a tac promoter for inducible expression, internal lac I$^q$ gene for use in any E. Coli host, and a coding region for thrombin cleavage—obtained from Pharmacia Biotech) which was used to amplify amino acids 792–928. This sequence was again cloned into pGEX 2T.

The retinoblastoma 792–928 sequence so obtained was expressed in E. Coli (BL21 (DE3) pLysS cells) using standard inducible expression techniques, and purified as follows.

E. coli paste was resuspended in 10 ml/g of NETN buffer (50 mM Tris pH 7.5, 120 mM NaCl, 1 mM EDTA, 0.5% v/v NP-40, 1 mM PMSF, 1 ug/ml leupeptin, 1 ug/ml aprotinin and 1 ug/ml pepstatin) and sonicated for 2×45 seconds per 100 ml homogenate. After centrifugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM MgCl2, 1 mM DTT, 1 mM PMSF, 1 ug/ml leupeptin, 1 ug/ml aprotinin and 1 ug/ml pepstatin) the protein was eluted with 50 mM reduced glutathione in kinase buffer. Fractions containing GST-Rb(792–927) were pooled and dialysed overnight against kinase buffer. The final product was analysed by Sodium Dodeca Sulfate (SDS) PAGE (Polyacrylamide gel) using 8–16% Tris-Glycine gels (Novex, San Diego, USA).

CDK2 and Cyclin E

The open reading frames of CDK2 and Cyclin E were isolated by reverse transcriptase-PCR using HeLa cell and activated T cell mRNA as a template and cloned into the insect expression vector pVL1393 (obtained from Invitrogen 1995 catalogue number: V1392–20). CDK2 and cyclin E were then dually expressed [using a standard virus Baculogold co-infection technique] in the insect SF21 cell system (*Spodoptera Frugiperda* cells derived from ovarian tissue of the Fall Army Worm—commercially available).

Example Production of Cyclin E/CDK2

The following Example provides details of the production of Cyclin E/CDK2 in SF21 cells (in TC100+10% FBS (TCS)+0.2% Pluronic) having dual infection MOI 3 for each virus of Cyclin E & CDK2.

SF21 cells grown in a roller bottle culture to $2.33\times10^6$ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

The viruses were mixed together before addition to the cultures, and the cultures returned to the roller rig 28° C.

After 2 days (48 hrs.) post infection the 5 Litres of culture was harvested. The total cell count at harvest was 1.58×10E6 cells/ml. (99% viable). The cells were spun out at 2500 rpm, 30 mins., 4° C. in Heraeus Omnhige 2.0 RS in 250 ml. lots. The supernatant was discarded.

Partial Co-Purification of Cdk2 and Cyclin E

Sf21 cells were resuspended in lysis buffer (50 mM Tris pH 8.2, 10 mM $MgCl_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homgeniser. After centrifugation, the supernatant was loaded onto a Poros HQ/M 1.4/100 anion exchange column (PE Biosystems, Hertford, UK). Cdk2 and Cyclin E were coeluted at the beginning of a 0–1M NaCl gradient (run in lysis buffer minus protease inhibitors) over 20 column volumes. Co-elution was checked by western blot using both anti-Cdk2 and anti-Cyclin E antibodies (Santa Cruz Biotechnology, California, US).

By analogy, assays designed to assess inhibition of CDK4 and CDK6 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

Although the pharmacological properties of the compounds of the formula (I) vary with structural change, in general activity possessed by compounds of the formula (I) may be demonstrated at $IC_{50}$ concentrations or doses in the range 250 $\mu$M to 1 nM.

The in vivo activity of the compounds of the present invention may be assessed by standard techniques, for example by measuring inhibition of cell growth and assessing cytotoxicity.

Inhibition of cell growth may be measured by staining cells with Sulforhodamine B (SRB), a fluorescent dye that stains proteins and therefore gives an estimation of amount of protein (i.e. cells) in a well (see Boyd, M. R. (1989) Status of the NCI preclinical antitumour drug discovery screen. Prin. Prac Oncol 10:1–12). Thus, the following details are provided of measuring inhibition of cell growth:-

Cells were plated in appropriate medium in a volume of 100 ml in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DMSO (v/v). A control plate was assayed to give a value for cells before dosing. Cells were incubated at 37° C., (5% $CO_2$) for three days.

At the end of three days TCA was added to the plates to a final concentration of 16% (v/v). Plates were then incubated at 4° C. for 1 hour, the supernatant removed and the plates washed in tap water. After drying, 100 ml SRB dye (0.4% SRB in 1% acetic acid) was added for 30 minutes at 37° C. Excess SRB was removed and the plates washed in 1% acetic acid. The SRB bound to protein was solubilised in 10 mM Tris pH7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical $IC_{50}$ values for compounds of the invention when tested in the SRB assay are in the range 1 mM to 1 nM.

According to a further aspect of the invention there is provided a pharmaceutical composition which comprises a compound of formula (I), or a pharmaceutically acceptable salt or in vivo hydrolysable ester thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt or in vivo hydrolysable ester thereof, as defined hereinbefore for use in a method of treatment of the human or animal body by therapy.

We have found that the compounds defined in the present invention, or a pharmaceutically acceptable salt or in vivo hydrolysable ester thereof, are effective cell cycle inhibitors (anti-cell proliferation agents), which property is believed to arise from their CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds may be used to produce an anti-proliferative effect mediated alone or in part by the inhibition of CDKs. Such a compound of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a compound of the invention will possess anti-cancer activity against these cancers. It is in addition expected that a compound of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDKs, especially those tumours which are significantly dependent on CDKs for their growth and spread, including for example, certain tumours of the colon, breast, prostate, lung, vulva and skin.

It is further expected that a compound of the present invention will possess activity against other cell-proliferation diseases in a wide range of other disease states including leukaemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a compound of the formula (I), or a pharmaceutically acceptable salt or in vivo hydrolysable ester thereof, as defined hereinbefore for use as a medicament; and the use of a compound of the formula (I), or a pharmaceutically acceptable salt or in vivo hydrolysable ester thereof, as defined hereinbefore in the manufacture of a medicament for use in the production of a cell cycle inhibitory (anti-cell-proliferation) effect in a warm-blooded animal such as man. Particularly, an inhibitory effect is produced by preventing entry into or progression through the S phase by inhibition of CDK2, CDK4 and/or CDK6, especially CDK2.

According to a further feature of the invention there is provided the use of a compound of the formula (I), or a pharmaceutically acceptable salt or in vivo hydrolysable ester thereof, as defined hereinbefore in the manufacture of a medicament for use in the treatment of cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, particularly in the treatment of cancers.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound as defined immediately above. Particularly, an inhibitory effect is produced by preventing entry into or progression through the S phase by inhibition of CDK2, CDK4 and/or CDK6, especially CDK2.

According to an additional feature of this aspect of the invention there is provided a method of treating cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal, such as man, in need of such treatment which comprises administering to said animal an effective amount of a compound of formula (I) or a pharmaceutically acceptable salt or in vivo hydrolysable ester thereof as defined hereinbefore.

Particularly there is provided a method of treating cancer in a warm-blooded animal, such as man, in need of such treatment which comprises administering to said animal an effective amount of a compound of formula (I) or a pharmaceutically acceptable salt or in vivo hydrolysable ester thereof as defined hereinbefore.

In a further aspect of the invention there is provided a pharmaceutical composition which comprises a compound of the formula (I), or a pharmaceutically acceptable salt or in vivo hydrolysable ester thereof, as defined hereinbefore in association with a pharmaceutically-acceptable diluent or carrier for use in the production of a cell cycle inhibitory (anti-cell-proliferation) effect in a warm-blooded animal such as man.

In a further aspect of the invention there is provided a pharmaceutical composition which comprises a compound of the formula (I), or a pharmaceutically acceptable salt or in vivo hydrolysable ester thereof, as defined hereinbefore in association with a pharmaceutically-acceptable diluent or carrier for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal such as man.

In a further aspect of the invention there is provided a pharmaceutical composition which comprises a compound of the formula (I), or a pharmaceutically acceptable salt or in vivo hydrolysable ester thereof, as defined hereinbefore in association with a pharmaceutically-acceptable diluent or carrier for use in the treatment of cancer in a warm-blooded animal such as man.

In a further aspect of the invention there is provided a compound of formula (I), or a pharmaceutically acceptable salt or in vivo hydrolysable ester thereof, as defined hereinbefore, for use in the production of a cell cycle inhibitory (anti-cell-proliferation) effect in a warm-blooded animal such as man.

In a further aspect of the invention there is provided a compound of the formula (I), or a pharmaceutically acceptable salt or in vivo hydrolysable ester thereof, as defined hereinbefore for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal such as man.

In a further aspect of the invention there is provided a compound of the formula (I), or a pharmaceutically acceptable salt or in vivo hydrolysable ester thereof, as defined hereinbefore for use in the treatment of cancer in a warm-blooded animal such as man.

Preventing cells from entering DNA synthesis by inhibition of essential S-phase initiating activities such as CDK2 initiation may also be useful in protecting normal cells of the body from toxicity of cycle-specific pharmaceutical agents. Inhibition of CDK2 or 4 will prevent progression into the cell cycle in normal cells which could limit the toxicity of cycle-specific pharmaceutical agents which act in S-phase, G2 or mitosis. Such protection may result in the prevention of hair loss normally associated with these agents.

Therefore in a further aspect of the invention there is provided a compound of formula (I) as defined above or a pharmaceutically acceptable salt or in vivo hydrolysable ester thereof for use as a cell protective agent.

Therefore in a further aspect of the invention there is provided a compound of formula (I) as defined above or a pharmaceutically acceptable salt or in vivo hydrolysable ester thereof for use in preventing hair loss arising from the treatment of malignant conditions with pharmaceutical agents.

Examples of pharmaceutical agents for treating malignant conditions that are known to cause hair loss include alkylating agents such as ifosfamide and cyclophosphamide; antimetabolites such as methotrexate, 5-fluorouracil, gemcitabine and cytarabine; vinca alkaloids and analogues such as vincristine, vinbalstine, vindesine, vinorelbine; taxanes such as paclitaxel and docetaxel; topoisomerase I inhibitors such as irintotecan and topotecan; cytotoxic antibiotics such as doxorubicin, daunorubicin, mitoxantrone, actinomycin-D and mitomycin; and others such as etoposide and tretinoin.

In another aspect of the invention, the compound of formula (I), or a pharmaceutically acceptable salt or in vivo hydrolysable ester thereof, may be administered in association with a one or more of the above pharmaceutical agents. In this instance the compound of formula (I) may be administered by systemic or non systemic means. Particularly the compound of formula (I) my may administered by non-systemic means, for example topical administration.

Therefore in an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof.

In an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof in simultaneous, sequential or separate administration with an effective amount of said pharmaceutical agent.

According to a further aspect of the invention there is provided a pharmaceutical composition for use in preventing hair loss arising from the treatment of malignant conditions with pharmaceutical agents which comprises a compound of formula (I), or a pharmaceutically acceptable salt or in vivo hydrolysable ester thereof and said pharmaceutical agent, in association with a pharmaceutically acceptable diluent or carrier.

According to a further aspect of the present invention there is provided a kit comprising a compound of formula (I), or a pharmaceutically acceptable salt or in vivo hydrolysable ester thereof, and a pharmaceutical agent for treating malignant conditions that is known to cause hair loss.

According to a further aspect of the present invention there is provided a kit comprising:

a) a compound of formula (I), or a pharmaceutically acceptable salt or in vivo hydrolysable ester thereof, in a first unit dosage form;
b) a pharmaceutical agent for treating malignant conditions that is known to cause hair loss; in a second unit dosage form; and
c) container means for containing said first and second dosage forms.

According to another feature of the invention there is provided the use of a compound of the formula (I), or a pharmaceutically acceptable salt or in vivo hydrolysable ester thereof, in the manufacture of a medicament for the prevention of hair loss during treatment of malignant conditions with pharmaceutical agents.

According to a further aspect of the present invention there is provided a combination treatment for the prevention of hair loss comprising the administration of an effective amount of a compound of the formula (I), or a pharmaceutically acceptable salt or in vivo hydrolysable ester thereof, optionally together with a pharmaceutically acceptable diluent or carrier, with the simultaneous, sequential or separate administration of an effective amount of a pharmaceutical agent for treatment of malignant conditions to a warm-blooded animal, such as man.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The CDK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, anti-androgens (for example flutamide, nilutamide, bicalutamide, cyproterone acetate), LBH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan). According to this aspect of the invention there is provided a pharmaceutical product comprising a compound of the formula (I) as defined hereinbefore and an additional anti-tumour substance as defined hereinbefore for the conjoint treatment of cancer.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C.;
(ii) organic-solutions were dried over anhydrous magnesium sulphate; evaporation of solvent was carried out using a rotary evaporator under reduced pressure (600–4000 Pascals; 4.5–30 mmHg) with a bath temperature of up to 60° C.;
(iii) chromatography means flash chromatography on silica gel; thin layer chromatography (TLC) was carried out on silica gel plates; where an amino isolute column is referred to, this means a column containing 10 g of $NH_2$ SPE sorbent of 40 micron particle size, the sorbent being contained in a 60 ml disposable syringe and supported by a porous disc, obtained from IST, Mid Glamorgan, UK under the name "Isolute NH2", "Isolute" is a trademark;
(iv) in general, the course of reactions was followed by TLC and reaction times are given for illustration only;
(v) final products had satisfactory proton nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated;
(viii) chemical symbols have their usual meanings; SI units and symbols are used;
(ix) solvent ratios are given in volume:volume (v/v) terms; and
(x) mass spectra were run with an electron energy of 70 electron volts in the chemical ionization (CD mode using a direct exposure probe; where indicated ionization was effected by electron impact (EI), fast atom bombardment (FAB) or electrospray (ESP); values for m/z are given; generally, only ions which indicate the parent mass are reported;
(xi) unless stated otherwise compounds containing an asymmetrically substituted carbon and/or sulphur atom have not been resolved;
(xii) where a synthesis is described as being analogous to that described in a previous example the amounts used are the millimolar ratio equivalents to those used in the previous example;
(xvi) the following abbreviations have been used:

| | |
|---|---|
| DMF | N,N-dimethylformamide; |
| DMFDMA | N,N-dimethylformamidedimethylacetyl; |
| DMSO | dimethylsulphoxide; and |
| THF | tetrahydrofuran. |

Example 1

2-(4-Sulphamoylanilino)-4-(imidazo[1,2a]pyrazin-3-yl) pyrmidine

Thionyl chloride (4 ml) and then DMF (5 μl) were added to 2-(4-sulphonoylanilino)-4-(imidazo[1,2a]pyrazin-3-yl) pyrmidine (Method 4; 75 mg, 0.204 mmol) under nitrogen and the mixture was stirred at ambient temperature for 48 hours. The volatiles were removed by evaporation and methanolic ammonia (6 ml of a 7M solution) was added directly to the residue under nitrogen and the mixture stirred for 1 hour at ambient temperature. The volatiles were removed by evaporation, and the residue purified by preparative HPLC (on a Gilson, 1" C18 column with gradient elution of 0.01% TFA buffered acetonitrile/water 5% to 50% over 10 minutes and 50% to 95% over 3.5 minutes). Fractions containing product were combined and lyophilised to give the title compound (17 mg, 23%) as a white solid. NMR: 7.20 (s, 2H), 7.60 (d, 1H), 7.72 (d, 2H), 7.95 (d, 2H), 8.18 (d, 1H), 8.62 (d, 1H), 8.85 (s, 1H), 9.28 (s, 1H), 10.01 (s, 1H), 10.20 (s, 1H); m/z: 368 $[MH]^+$.

Example 2
2-(4-{N-[2-(Dimethylamino)ethyl]sulphamoyl}anilino)-4-(imidazo[1,2a]pyrazin-3-yl)pyrimidine 2-(4-Sulphonoylanilino)-4-(imidazo[1,2a]pyrazin-3-yl)pyrimidine (Method 4; 67 mg, 0.181 mmol) was dissolved in acetonitrile (1 ml) and sulfolane (1 ml) and stirred under nitrogen. Phosphoryl chloride (67 µl, 0.724 mmol) and N,N-dimethylacetamide (10 µl) were added. The reaction mixture was heated under reflux for 30 minutes, allowed to cool and the volatiles removed by evaporation. The resulting solution was placed under nitrogen and an anhydrous solution of triethylamine (252 µl, 1.81 mmol) and 1,1-dimethylethyldiamine (40 µl, 0.362 mmol) in methanol (2 ml) was added slowly. The mixture was left at ambient temperature for 30 minutes, then dichloromethane (15 ml) and water (15 ml) were added. The aqueous layer was separated and adjusted to pH 9 by careful addition of 2M aqueous sodium hydroxide solution. The resulting precipitate was collected by filtration, washed with water (2×15 ml) and ether (3×15 ml) and dried over phosphorus pentoxide for 16 hours to give the title compound (16 mg, 20%). NMR: 2.1 (s, 6M), 2.3 (t, 2H), 2.8 (t, 21), 7.3 (br s, 1H), 7.5 (d, 1H), 7.75 (d, 2H), 7.95 (d, 2H), 8.2 (d, 1H), 8.6 (d, 1H), 8.8 (s, 1H), 9.3 (s, 1H), 9.95 (d, 1H), 10.2 (s, 1H); m/z: 440 [MH]$^+$.

Example 3
2-{4-[N-(2-Methoxyethyl)sulphamoyl]anilino}-4-(imidazo[1,2a]pyrazin-3-yl)pyrimidine Thionyl chloride (6 ml) and DMF (10 µl) were added to 2-(4-sulphonoylanilino)-4-(imidazo[1,2a]pyrazin-3-yl)pyrimidine (Method 4; 110 mg, 0.299 mmol) under and the mixture was stirred at ambient temperature for 12 hours. The volatiles were removed by evaporation and the residue placed under nitrogen. Anhydrous pyridine (7 ml) followed by 2-methoxyethylamine (26 µl, 0.299 mmol) was added directly and the mixture stirred at ambient temperature for 3 hours. The volatiles were removed by evaporation, and the residue purified by column chromatography eluting with dichloromethane/methanol (100:0 increasing in polarity to 95:5) to give the title compound (6 mg, 5%) as a white solid. NMR: 2.9 (t, 2H), 3.2 (s, 3H), 3.4 (t, 2H), 7.5 (t, 1H), 7.7 (d, 1H) 7.8 (d, 2H) 7.95 (d, 2H), 8.2 (d, 1H), 8.6 (d, 1H), 8.9 (s, 1H), 9.3 (s, 1H), 10.0 (d,1H) 10.2 (s, 1H); m/z: 426 [MH]$^+$.

Example 4
2-{4-[N-(2-Methoxyethyl)sulphamoyl]anilino}-4-(imidazol[1,2a]pyrimidin-3-yl)pyrimidine 2-[4-Sulphonoylanilino]-4-(imidazo[1,2a]pyrimidin-3-yl)pyrimidine (Method 8; 180 mg, 0.49 mmol) was dissolved in acetonitrile (1 ml) and sulfolane (1 ml) and stirred under nitrogen. Phosphoryl chloride (136 µl, 1.46 mmol) and N,N-dimethylacetamide (1.8 µl) were added and the reaction mixture was stirred at ambient temperature for 4 hours then heated under reflux for 30 minutes, allowed to cool and the volatiles removed by evaporation. The resulting solution was placed under nitrogen and a solution of 2-methoxyethylamine (85 µl, 0.978 mmol), triethylamine (204 ml, 1.47 mmol) in methanol (5 ml) was added and the mixture stirred at ambient temperature for 1 hour. The resulting solid was collected by filtration, washed with ether (3×20 ml), and dried to give the title compound (89 mg, 43%). NMR: 2.9. (dd, 1H), 3.08 (m, 2H), 3.18 (s, 3H), 3.3 (t, 2H), 7.56 (d, 1H) 7.77 (d, 2H) 7.98 (d, 2H), 8.6 (d, 1H), 8.86 (dd, 1H), 8.98 (s, 1H), 10.3 (s,1H) 10.54 (s, 1H); m/z: 426 [MH]$^+$.

Example 5
2-(4-sulphamoylanilino)-4-(imidazo[1,2b]pyridazin-3-yl)pyrimidine

2-Anilino-4-(imidazo[1,2b]pyridazin-3-yl)pyrimidine (Example 10; 100 mg, 0.347 mmol) was dissolved in thionyl chloride (2.0 ml) and the solution stirred and cooled to 0° C. Chlorosulphonic acid (92 µl, 1.39 mmol) was added and the reaction was stirred at 0° C. for 30 minutes and then at ambient temperature for 1 hour and finally heated at 80° C. for 90 minutes. The mixture was allowed to cool and the volatiles were removed by evaporation. 2M methanolic ammonia (6.0 ml) was added to the residue in the flask and the mixture stirred at ambient temperature for 1 hour. The volatiles were removed by evaporation and distilled water added to the residue and the mixture stirred for 30 minutes. The precipitate was collected by filtration, washed with water and dried. The crude product was triturated with dichloromethane containing a trace of methanol, collected by filtration washed with dichloromethane/methanol and dried to give the title compound (81 mg, 64%) as a white solid. NMR: 7.1 (s, 2H), 7.45 (d, 1H), 7.8 (d, 2H), 8.03 (m, 3H), 8.32 (d, 1H), 8.64 (m, 2H), 8.8 (d, 1H); 10.05 (s, 1H); m/z: 368 [MH]$^+$.

Example 6
2-[4-(N-Methylsulphamoyl)anilino]-4-(imidazo[1,2b]pyridazin-3-yl)pyrimidine 2-Anilino-4-(imidazo[1,2b]pyridazin-3-yl)pyrimidine (Example 10; 100 mg, 0.347 mmol) was treated by the method described in Example 5 to give the crude sulphonyl chloride which was treated with 2.0M solution of methylamine in methanol (6.0 ml) and the reaction worked-up as described in Example 5 to give the title compound (78 mg, 59%) as a white solid. NMR: 2.4 (d, 3H), 7.16 (q, 1H), 7.45 (dd, 1H), 7.75 (d, 2H), 8.07 (m, 3H), 8.33 (d, 1H), 8.67 (m, 2H), 8.8 (d, 1H); 10.11 (s, 1H); m/z: 380 [M–H]$^-$.

Example 7
2-{4-[N-(2-Methoxyethyl)sulphamoyl]anilino}-4-(imidazo[1,2b]pyridazin-3-yl)pyrimidine 2-Anilino-4-(imidazo[1,2b]pyridazin-3-yl)pyrimidine (Example 10; 100 mg, 0.347 mmol) was treated by the method described in Example 5 to give the crude sulphonyl chloride which was treated with a solution of 2-methoxyethylamine (0.452 ml) in methanol (1.0 ml) and the reaction worked-up as described in Example 5 to give the title compound (39 mg, 26%) as a white solid. NMR (DMSO d6+d4 Acetic acid): 2.87 (t, 2H), 3.15 (s, 3H), 3.27 (t, 2H), 7.4 (dd, 1H), 7.74 (d, 2H), 8.05 (m, 3H), 8.3 (d, 1H), 8.64 (m, 2H), 8.76 (d, 1H). m/z: 424 [M–H]$^-$.

Example 8
2-[4-(N-(3-Dimethylaminpropyl)sulphamoyl)anilino]-4-(imidazo[1,2b]pyridazin-3-yl)pyrimidine 2-Anilino-4-(imidazo[1,2b]pyridazin-3-yl)pyrimidine (Example 10; 100 mg, 0.347 mmol) was treated by the method described in Example 5 to give the crude sulphonyl chloride which was treated with a solution of 3-dimethylaminopropylamine (87 µl), dimethylethylamine (2.16 ml) in methanol (4.0 ml) and the resulting suspension stirred at ambient temperature for 90 minutes. Volatiles were removed by evaporation, distilled water was added to the residue and the mixture stirred for 30 minutes. The resulting precipitate was collected by filtration, washed with distilled water and dried. The crude product dissolved in DMF was purified on a 10 g amino isolute column prequilibrated with methanol. The product was eluted with methanol, the purified product was triturated with ether/ethyl acetate, collected by filtration, washed with ether and dried to the title compound (53 mg, 26%) as a white solid. NMR: 1.48 (m, 2H), 2.03 (s, 6H), 2.13 (t, 2H), 2.75 (t, 2H), 7.33 (s, 1H), 7.45 (dd, 1H), 7.73 (d, 2H), 8.07 (m, 3H), 8.33 (d, 1H), 8.65 (s, 1H), 8.68 (d, 1H), 8.8 (d, 1H), 10.11 (s, 1H); m/z: 451 [M–H]−.

Example 9

2-Anilino-4-(imidazo[1,2a]pyrazin-3-yl)pyrimidine 3-(3-Dimethylaminoprop-2-en-1-oyl)imidazo[1,2a]pyrazine (Method 3; 400 mg, 1.85 mmol), phenyl guanidine hydrogencarbonate (365 mg, 1.85 mmol) and sodium methoxide (199 mg, 3.7 mmol) were dissolved in anhydrous dimethylacetamide (15 ml) and the mixture heated under reflux at 160° C. under nitrogen for 2 hours. The reaction mixture was allowed to cool, acetic acid (212 µl, 3.7 mmol) was added and the mixture poured carefully on to ice-water (40 ml). The ice was allowed to melt and the aqueous solution extracted with dichloromethane (2×20 ml). The extracts were combined, dried and the solvent removed by evaporation to give title compound (392 mg, 72%) as a brown solid. NMR: 7.0 (t, 1H), 7.35 (t, 2H), 7.48 (d, 1H), 7.75 (d, 2H), 8.1 (d, 1H), 8.52 (d, 1H), 8.88 (s, 1H), 9.21 (s, 1H), 9.86 (s, 1H), 9.98 (d, 1H), m/z: 299 [MH]+.

Example 10

2-Anilino-4-(imidazo[1,2b]pyridazin-3-yl)pyrimidine 3-(3-Dimethylaminoprop-2-en-1-oyl)imidazo[1,2b]pyridazine (Method 17; 600 mg, 2.78 mmol), phenyl guanidine hydrogen carbonate (603 mg, 3.06 mmol) and sodium methoxide (300 mg, 5.56 mmol) were suspended in dry dimethyl acetamide (25 ml) under nitrogen and the mixture was stirred and heated at 160° C. for 2 hours. The reaction was then stirred at room temperature for 20 hours and then further phenyl guanidine hydrogen carbonate (273 mg) and sodium methoxide (150 mg) were added and the reaction heated at 160° C. for 2 hours. The reaction was allowed to cool to ambient temperature and acetic acid (0.5 ml) added and the volatiles removed by evaporation. Water was added to the residue and the resulting suspension stirred for 30 minutes. The product was collected by filtration, washed with water and dried to give the title compound (705 mg, 88%) as a brown solid. NMR: 6.96 (t, 1H), 7.33 (m, 2H), 7.42 (dd, 1H), 7.85 (d, 2H), 7.97 (d, 1H), 8.30 (d, 1H), 8.55 (s, 1H), 8.61 (d, 1H), 8.77 (d, 1H), 9.63 (s, 1H). m/z: 289 MH]+.

Example 11

2-Anilino-4-(imidazo[1,2a]pyrimidin-3-yl)pyrimidine 3-(3-Dimethylaminoprop-2-en-1-oyl)imidazo[1,2a]pyrimidine (Method 7; 450 mg, 2.08 mmol) was treated as described in Example 9 to give crude product which was triturated with ether to give the title compound as the major component (70%) in an isomeric mixture with 2-anilino-4-(imidazo[1,2a]pyrimidin-2-yl)pyrimidine (392 mg, 65%). NMR: 7.0 (t, 1H), 7.26 (dd, 1H), 7.34 (t, 2H), 7.73 (d, 2H), 8.46 (d, 1H), 8.69 (dd, 1H), 8.76 (s, 1H), 9.67 (s, 1H), 10.38 (d, 1H).

Example 12

2-(2-Fluoroanilino)-4-(imidazo[1,2b]pyridazin-3-yl)pyrimidine 3-(3-Dimethylaminoprop-2-en-1-oyl)imidazo[1,2b]pyridazine (Method 17, 1.0 g, 4.63 mmol), 2-fluorophenylguanidine hydrogen carbonate (Method 25; 1.1 g, 5.09 mmol) and sodium methoxide (550 mg, 10.2 mmol) were suspended in DMA (42 ml) and the mixture stirred and heated at 140° C. for 5.5 hours. The mixture was allowed to cool to ambient temperature and then acetic acid (0.33 ml) was added and the volatiles removed by evaporation. The residue was triturated with water and the product collected by filtration, washed with water and dried to give title compound (406 mg, 29%) as a brown solid. NMR: 7.13 (m, 1H), 7.2 (m, 2H), 7.4 (dd, 1H), 7.93. (m, 2H), 8.8 (d, 1H), 8.43 (s, 1H), 8.58 (d, 1H), 8.77 (d, 1H), 9.05 (s, 1H); m/z: 307 [MH]+.

Example 13

2-Anilino-4-(2-methylimidazo[1,2b]pyridazin-3-yl)pyrimidine 3-(3-Dimethylaminoprop-2-en-1-oyl)-2-methylimidazo[1,2b]pyridazine (Method 18; 1.5 g, 6.52 mmol), phenylguanidine hydrogen carbonate (1.41 g, 7.17 mmol) and sodium methoxide (704 mg, 13.04 mmol) were suspended in dimethylacetamide (62 ml) and the mixture stirred and heated at 160° C. for 2.5 hours. The mixture was allowed to cool and more phenylguanidine hydrogen carbonate (642 mg, 3.25 mmol) and sodium methoxide (352 mg, 6.52 mmol) were added and the reaction mixture heated a further 2 hours at 160° C. The mixture was allowed to cool to ambient temperature and acetic acid (1.16 ml) was added and the volatiles removed by evaporation. The triturated with water and the precipitated solid collected by filtration, washed with water, dried and recrystallized from methanol to give the title compound (785 mg, 40%) as a pale yellow solid. NMR: 2.77 (s, 3H), 6.95 (t, 1H), 7.27 (t, 2H), 7.35 (dd, 1H), 7.76 (d, 2H), 7.83 (d, 1H), 8.15 (d, 1H), 8.58 (d, 1H), 8.65 (d, 1H), 9.5 (s, 1H); m/z: 303 [MH]+.

Examples 14–19

The following compounds were prepared by methods analogous to that described in Example 13.

| Ex | Compound | NMR | M/z |
|---|---|---|---|
| 14[1] | 2-Anilino-4-(2-ethylimidazo[1,2b]pyridazin-3-yl)pyrimidine | 1.27(t, 3H), 3.27(q, 2H), 6.93(t, 1H), 7.27(m, 2H), 7.36(dd, 1H), 7.73(m, 3H), 8.17(d, 1H), 8.57(d, 1H), 8.65(d, 1H), 9.48(s, 1H) | 317 [MH]+ |
| 15[2] | 2-Anilino-4-(2-dimethylaminoimidazo[1,2b]pyridazin-3-yl)pyrimidine | 2.98(s, 6H), 6.93(t, 1H), 7.25(m, 3H), 7.57(d, 1H), 7.9(m, 3H), 8.45 (d, 1H), 8.52(d, 1H), 9.55(s, 1H) | 332 [MH]+ |
| 16 | 2-Anilino-4-(5-methoxyimidazo[1,2b]pyridazin-3-yl)pyrimidine | 4.1(s, 3H), 6.95(t, 1H), 7.08(d, 1H), 7.32(t, 2H), 7.82(d, 2H), 8.0 | 319 [MH]+ |

-continued

| Ex | Compound | NMR | M/z |
|----|----------|-----|-----|
| 17 | 2-Anilino-4-(5-(2,2,2-trifluorethoxy) imidazo[1,2b]pyridazin-3-yl)pyrimidine | (d, 2H), 8.18(d, 1H), 8.40(s, 1H), 8.60(d, 1H), 9.60(s, 1H) 5.18(q, 2H), 6.95(t, 1H), 7.22(d, 1H), 7.32(t, 2H), 7.82(d, 2H), 7.92 (d, 1H), 8.26(d, 1H), 8.42(s, 1H), 8.61(d, 1H), 9.6(s, 1H) | 387 [MH]+ |
| 18 | 2-Anilino-4-(6,7-dimethylimidazo[1,2b]pyridazin-3-yl)pyrimidine | 2.39(s, 3H), 2.58(s, 3H), 6.95(t, 1H), 7.34(t, 2H), 7.88(d, 2H), 7.92 (d, 1H), 8.45(s, 1H), 8.58(m, 2H), 9.58(s, 1H) | 317 [MH]+ |
| 19 | 2-Anilino-4-(6-methylimidazo[1,2b]pyridazin-3-yl)pyrimidine | 2.45(s, 3H), 6.96(t, 1H), 7.32(t, 2H), 7.87(d, 2H), 7.92(d, 1H), 8.08(s, 1H), 8.48(s, 1H), 8.58 (d, 1H), 9.48(s, 1H) | 303 [MH]+ |

[1]Purified by chromatography eluting with dichloromethane/methanol (98.5:1.5) NMR:; m/z:.
[2]Purified by chromatography eluting with dichloromethane/methanol (98:2)

Example 20
2-{2-Fluoro-4-[N-(2-methoxyethyl)sulphamoyl]anilino}-4-(imidazo[1,2b]pyridazin-3-yl)pyrimidine Chlorosulphonic acid (109 μl, 1.64 mmol) was added to a stirred solution of 2-(2-fluoroanilino)-4-(imidazo[1,2b]pyridazin-3-yl)pyrimidine (Example 12; 130 mg, 0.41 mmol) in thionyl chloride (2.6 ml) cooled to 0° C. The reaction was stirred at 0° C. for 5 minutes, then heated at 90° C. for 80 minutes, allowed to cool and the volatiles removed by evaporation. 2-Methoxyethylamine (0.75 ml, 8.58 mmol) in methanol (2.0 ml) was added to the residue and the mixture stirred at ambient temperature for 20 hours. The volatiles were removed by evaporation, water added to the residue and the mixture stirred for 30 minutes. The resulting precipitate was collected by filtration, washed with water and dried to give the title compound (217 mg, 86%) as a white solid. NMR: 2.94 (t, 2H), 3.17 (s, 3H), 3.28 (t, 2H), 7.43 (dd, 1H), 7.65 (dd, 3H), 8.06 (d, 1H), 8.32 (d, 1H), 8.41 (t, 1H), 8.55 (s, 1H), 8.66 (d, 1H), 8.78 (d, 1H), 9.45 (s, 1H); m/z: 444 [MH]+.

Example 21
2-(2-Fluoro-4-sulphamoylanilino)-4-(imidazo[1,2b]pyridazin-3-yl)pyrimidine 2-(2-Fluoroanilino)-4-(imidazo[1,2b]pyridazin-3-yl)pyrimidine (Example 12; 175 mg, 0.572 mmol) was treated by the method in Example 20 and reacted with a 2.0M solution of ammonia in methanol (4.3 ml) to give the title compound (112 mg, 51%) as a white solid. NMR: 7.33 (s, 2H), 7.45 (dd, 1H), 7.67 (m, 2H), 8.07 (d, 1H), 8.33 (m, 2H), 8.53 (s, 1H), 8.66 (d, 1H), 8.8 (d, 1H), 9.45 (s, 1H); m/z: 386 [MH]+.

Examples 22–26

The following compounds were prepared by a method analogous to that described in Example 21.

| Ex | Compound | NMR | M/z |
|----|----------|-----|-----|
| 22[1] | 2-(4-Sulphamoylanilino)-4-(2-methylimidazo[1,2b]pyridazin-3-yl)pyrimidine | 2.82(s, 3H), 7.13(s, 2H), 7.37(dd, 1H), 7.73(d, 2H), 7.9(d, 1H), 7.97 (d, 2H), 8.16(d, 1H), 8.65(m, 2H), 9.97(s, 1H) | 380 [M-H]− |
| 23[2] | 2-(4-Sulphamoylanilino)-4-(2-ethylimidazo[1,2b]pyridazin-3-yl)pyrimidine | 1.30(t, 3H), 3.27(q, 2H), 7.13(s, 2H), 7.38(dd, 1H), 7.73(d, 2H), 7.87(d, 1H), 7.95(d, 2H), 8.2(d, 1H), 8.65(m, 2H), 9.97(s, 1H) | 396 [MH]+ |
| 24[3] | 2-(4-Sulphamoylanilino)-4-(5-methoxyimidazo[1,2b]pyridazin-3-yl)pyrimidine | 4.19(s, 3H), 7.09(d, 1H), 7.13(s, 2H), 7.78(d, 2H), 8.0(d, 2H), 8.06 (d, 1H), 8.2(d, 1H), 8.43(s, 1H), 8.68(d, 1H) | 398 [MH]+ |
| 25[4] | 2-(4-Sulphamoylanilino)-4-(5-(2,2,2-trifluorethoxy)imidazo[1,2b]pyridazin-3-yl)pyrimidine | 5.2(q, 2H), 7.15(s, 2H), 7.24(d, 1H), 7.78(d, 2H), 7.98(d, 2H), 8.02(d, 1H), 8.3(d, 1H), 8.5(s, 1H), 8.7(d, 1H), 10.04(s, 1H) | 466 [MH]+ |
| 26 | 2-(4-Sulphamoylanilino)-4-(6,7-dimethylimidazo[1,2b]pyridazin-3-yl)pyrimidine | 2.38(s, 3H), 2.47(s, 3H), 7.12(s, 2H), 7.78(d, 2H), 7.97(d, 1H), 8.0 (d, 2H), 8.5(s, 1H), 8.6s(s, 1H), 8.65(d, 1H), 10.02(s, 1H) | 396 [MH]+ |

[1]Purified by chromatography on a amine Isolute column eluting with methanol/dichloromethane (1:1)
[2]Purified by trituration with dichloromethane/methanol
[3]Purified by chromatography on silica gel chromatography eluting with dichloromethane/methanol (99:1) increasing polarity to (80:20)
[4]Purified by chromatography a 10 g amino Isolute column eluting with dichloromethane/methanol (1:1)

Examples 27–38

The following compounds were prepared by a method analogous to that described in Example 20.

| Ex | Compound | NMR | M/z |
|---|---|---|---|
| 27 | 2-{4-[N-(2-Methoxyethyl) sulphamoyl]anilino}-4-(2-methylimidazo[1,2b]pyridazin-3-yl)pyrimidine | (DMSOd$_6$/CD$_3$CO$_2$D): 2.8(s, 3H), 2.87 (t, 2H), 3.15(s, 3H), 3.3(t, 2H), 7.36(dd, 1H), 7.7(d, 2H), 7.92(d, 1H), 7.98(d, 2H), 8.15(d, 1H), 8.64(m, 2H), 9.97(s, 1H) | 438 [M-H]$^-$ |
| 28 | 2-{4-[N-(3-Dimethylaminopropyl) sulphamoyl]anilino}-4-(2-methylimidazo[1,2b]pyridazin-3-yl)pyrimidine | 1.47(m, 2H), 2.03(s, 6H), 2.13(t, 2H), 2.73(t, 2H), 2.8(s, 3H), 7.36(m, 2H), 7.67(d, 2H), 7.92(d, 1H), 8.0(d, 2H), 8.17(d, 1H), 8.67(m, 2H), 10.0(s, 1H) | 465 [M-H]$^-$ |
| 29 | 2-[4-(N-Methylsulphamoyl) anilino]-4-(2-methylimidazo[1,2b] pyridazin-3-yl)pyrimidine | 2.4(d, 3H), 2.8(s, 3H), 7.17(q, 1H), 7.37 (dd, 1H), 7.67(d, 2H), 7.9(d, 1H), 8.0(d, 2H), 8.16(d, 1H), 8.65(m, 2H), 10.0(s, 1H) | 394 [M-H]$^-$ |
| 30 | 2-{4-[N-(2-Methoxyethyl) sulphamoyl]anilino}-4-(2-ethylimidazo[1,2b]pyridazin-3-yl)pyrimidine | 1.32(t, 3H), 2.87(t, 2H), 3.15(s, 3H), 3.27(m, 4H), 7.38(dd, 1H), 7.45(s, 1H), 7.7(d, 2H), 7.88(d, 1H), 7.98(d, 2H), 8.2 (d, 1H), 8.65(d, 2H), 10.0(s, 1H) | 453 [MH]$^+$ |
| 31 | 2-[4-(N-Methylsulphamoyl) anilino]-4-(2-ethylimidazo[1,2b] pyridazin-3-yl)pyrimidine | 1.33(t, 3H), 2.38(d, 3H), 3.25(q, 2H), 7.2(q, 1H), 7.38(dd, 1H), 7.68(d, 2H), 7.9(d, 1H), 7.98(d, 2H), 8.2(d, 1H), 8.63 (m, 2H), 9.97(s, 1H) | 410 [MH]$^+$ |
| 32[1] | 2-{4-[N-(2-Methoxyethyl) sulphamoyl]anilino}-4-(2-dimethylaminoimidazo[1,2b] pyridazin-3-yl)pyrimidine | 2.85(t, 2H), 2.97(s, 6H), 3.17(m, 5H), 7.3(dd, 1H), 7.45(t, 1H), 7.68(m, 3H), 7.97(dd, 1H), 8.1(d, 2H), 8.49(dd, 1H), 8.58(d, 1H), 10.08(s, 1H) | 469 [MH]$^+$ |
| 33[2] | 2-{4-[N-(2-Dimethylaminoethyl) sulphamoyl]anilino}-4-(5-methoxyimidazo[1,2b]pyridazin-3-yl)pyrimidine | 2.23(s, 6H), 2.82(t, 2H), 3.0(m, 2H), 4.08(s, 3H), 7.08(d, 1H), 7.58(br s, 1H), 7.98(d, 2H), 8.06(d, 2H), 8.1(d, 1H), 8.44(s, 1H), 8.68(d, 1H), 10.12(s, 1H) | 469 [MH]$^+$ |
| 34 | 2-[4-(N-Methylsulphamoyl) anilino]-4-(5-methoxyimidazo [1,2b]pyridazin-3-yl)pyrimidine | 2.41(d, 3H), 4.08(s, 3H), 7.08(d, 1H), 7.2(m, 1H), 7.73(d, 2H), 8.04(d, 2H), 8.08(d, 1H), 8.19(d, 1H), 8.45(s, 1H), 8.64(d, 1H), 10.07(br s, 1H) | 412 [MH]$^+$ |
| 35[3] | 2-{4-[N-(2-Methoxyethyl) sulphamoyl]anilino}-4-(5-methoxyimidazo[1,2b]pyridazin-3-yl)pyrimidine | 2.9(t, 2H), 3.18(s, 3H), 3.28(m, 2H) 4.1 (s, 3H), 7.12(d, 1H), 7.43(t, 1H), 7.76(d, 2H), 8.04(d, 2H), 8.1(d, 1H), 8.2(d, 1H), 8.43(s, 1H), 8.68(d, 1H), 10.07(s, 1H) | 456 [MH]$^+$ |
| 36 | 2-{4-[N-(3-Methoxypropyl) sulphamoyl]anilino}-4-(5-methoxyimidazo[1,2b]pyridazin-3-yl)pyrimidine | 1.6(quin, 2H), 2.78(q, 2H), 3.17(s, 3H), 3.25(t, 2H), 4.08(s, 3H), 7.08(d, 1H), 7.32(t, 1H), 7.75(d, 2H), 8.02(d, 2H), 8.08(d, 1H), 8.19(d, 1H), 8.46(s, 1H), 8.66(d, 1H), 10.07(s, 1H) | 470 [MH]$^+$ |
| 37[4] | 2-{4-[N-(2-Methoxyethyl) sulphamoyl]anilino}-4-(6,7-dimethylimidazo[1,2b]pyridazin-3-yl)pyrimidine | 2.37(s, 3H), 2.56(s, 3H), 2.9(t, 2H), 3.16 (s, 3H), 3.31(t, 2H), 7.35(t, 1H), 7.75(d, 2H), 8.01(d, 1H), 8.05(d, 2H), 8.52(s, 1H), 8.48(s, 1H), 8.64(d, 1H), 9.9(s, 1H) | 454 [MH]$^+$ |
| 38[5] | 2-{4-[N-(2-Methoxyethyl) sulphamoyl]anilino}-4-(6-methylimidazo[1,2b] pyridazin-3-yl)pyrimidine | 2.49(s, 3H), 2.92(q, 2H), 3.19(s, 3H), 3.34(q, 2H), 7.47(t, 1H), 7.78(d, 2H), 8.04(d, 1H), 8.09(d, 2H), 8.14(s, 1H), 8.6(s, 1H), 8.69(d, 1H), 8.74(d, 1H), 10.1(s, 1H) | 440 [MH]$^+$ |
| 39[6] | 2-{4-[N-(2-Ethoxyethyl) sulphamoyl]anilino}-4-(imidazo[1,2b]pyridazin-3-yl)pyrimidine | 1.04(t, 3H), 2.90(q, 2H), 3.35(m, 4H), 7.44(m, 2H), 7.76(d, 2H), 8.08(m, 3H), 8.36(d, 1H), 8.66(s, 1H), 8.70(d, 1H), 8.80(d, 1H), 10.11(s, 1H) | 440 [MH]$^+$ |

[1]Purified by reverse phase chromatography on a Hypersil BDS C18 21 × 100 mm column eluting with acetonitrile/water/trifluoroacetic acid (10:90:0.1) decreasing in polarity to (90:10:0.1)
[2]Triturated with methanol/ether/dichloromethane
[3]Purified by chromatography on silica gel eluting with dichloromethane/methanol (95:5) and then with dichloromethane/2M methanolic ammonia solution (95:5)
[4]Triturated with methanol
[5]Purified by chromatography on silica gel eluting with dichloromethane/methanol (97:3)
[6]Purified by further trituration with methanol

Example 40
2-{4-[N-(1-Methylcycloprop-1-yl)sulphamoyl]anilino}-4-(imidazo[1,2b]pyridazin-3-yl)pyrimidine Chlorosulphonic acid (0.22 ml, 3.3 mmol) was added to a solution of 2-anilino-4-(imidazo[1,2b]pyridazin-3-yl)pyrimidine (Example 10; 300 mg, 1.04 mmol) in thionyl chloride (6 ml) cooled at 5° C. The mixture was stirred at 5° C. for 30 minutes, then at ambient temperature for 1.5 hours and then heated at reflux for 1.5 hours. 1-Amino-1-methylcyclopropane (Method 48; 2 ml) in isopropanol (10 ml) and dimethylethylamine (3 ml) was added and the mixture stirred at ambient temperature for 18 hours. The solvent was evaporated and the residue purified by chromatography on silica gel eluting with dichloromethane/isohexane (1:1) increasing in polarity to dichloromethane/methanol (95:5). The purified product was triturated with ether/methanol to give the title compound (89 mg, 21%). NMR: 0.16–0.19 (m, 2H), 0.40–0.44 (m, 2H), 0.92 (s, 3H), 7.25 (dd, 1H), 7.55–7.60 (m, 3H), 7.86–7.90 (m, 31), 8.15 (d, 1H), 8.48 (s, 1H), 8.53 (d, 1H), 8.62 (d, 1H), 9.95 (s, 1H); m/z: 422 [MH]$^+$.

Examples 41–57

The following compounds were prepared by a method analogous to that described in Example 40.

| Ex | Compound | NMR | M/z |
|---|---|---|---|
| 41 | 2-{4-[N-(3-Methoxypropyl)sulphamoyl]anilino}-4-(imidazo[1,2b]pyridazin-3-yl)pyrimidine | 1.58(quin, 2H), 2.78(q, 2H), 3.14(s, 3H), 3.22–3.25(m, 2H), 7.32(t, 1H), 7.44(dd, 1H), 7.75(d, 2H), 8.05(s, 1H), 8.16(d, 2H), 8.34(s, 1H), 8.63(s, 1H), 8.68(d, 1H), 8.8 (d, 1H), 10.12(s, 1H) | 440 [MH]$^+$ |
| 42 | 2-[4-(N-Propylsulphamoyl)anilino]-4-(imidazo[1,2b]pyridazin-3-yl)pyrimidine | 0.79(t, 3H), 1.38(q, 2H), 2.69(q, 2H), 7.32 (t, 2H), 7.45(dd, 1H), 7.75(d, 2H), 8.04(s, 1H), 8.09(d, 2H), 8.34(d, 1H), 8.63(s, 2H), 8.68(d, 1H), 8.80(d, 1H), 10.11(s, 1H) | 410 [MH]$^+$ |
| 43 | 2-[4-(N-Ethylsulphamoyl)anilino]-4-(imidazo[1,2b]pyridazin-3-yl)pyrimidine | 0.96(t, 3H), 2.78(q, 2H), 7.30(t, 1H), 7.43 (dd, 1H), 7.75(d, 2H), 8.05(s, 1H), 8.08(d, 2H), 8.35(d, 1H), 8.64(s, 1H), 8.69(d, 1H), 8.80(d, 1H), 10.11(s, 1H) | 396 [MH]$^+$ |
| 44 | 2-[4-(N-Allylsulphamoyl)anilino]-4-(imidazo[1,2b]pyridazin-3-yl)pyrimidine | 3.40(t, 2H), 5.01(d, 1H), 5.15(d, 1H), 5.61–5.70 (m, 1H), 7.45(dd, 1H), 7.56(t, 1H), 7.78 (d, 2H), 8.04(s, 1H), 8.07(d, 2H), 8.35(d, 1H), 8.64(s, 1H), 8.70(d, 2H), 8.80(d, 1H), 10.12(s, 1H) | 408 [MH]$^+$ |
| 45 | 2-[4-(N-Propargylsulphamoyl)anilino]-4-(imidazo[1,2b]pyridazin-3-yl)pyrimidine | 3.64(s, 2H), 7.44(dd, 1H), 7.78(d, 2H), 8.08 (m, 3H), 8.34(d, 1H), 8.70(d, 1H), 8.80(d, 1H), 10.13(s, 1H) | 406 [MH]$^+$ |
| 46 | 2-{4-[N-(2-(1-Pyrazolyl)ethyl)sulphamoyl]anilino}-4-(imidazo[1,2b]pyridazin-3-yl)pyrimidine | 3.11(q, 2H), 4.15(t, 2H), 6.20(s, 1H), 7.39 (s, 1H), 7.44(dd, 1H), 7.59(t, 1H), 7.65(s, 1H), 7.74(s, 2H), 8.08(s, 1H), 8.09(d, 2H), 8.32(d, 1H), 8.64(s, 1H), 8.69(d, 1H), 8.80 (d, 1H), 10.13(s, 1H) | 462 [MH]$^+$ |
| 47 | 2-{4-[N-(1,3-Dihydroxyprop-2-yl)sulphamoyl]anilino}-4-(imidazo[1,2b]pyridazin-3-yl)pyrimidine | 3.01–3.06(m, 1H), 3.25–3.35(m, 4H), 4.55(t, 2H), 7.18(d, 1H0, 7.49(dd, 1H), 7.80(dd, 2H), 8.04(s, 1H), 8.09(dd, 2H), 8.35(d, 1H), 8.68(s, 1H), 8.70(d, 1H), 8.80(d, 1H), 10.15 (s, 1H) | 442 [MH]$^+$ |
| 48 | 2-{4-[N-(1-Hydroxyprop-2-yl)sulphamoyl]anilino}-4-(imidazo[1,2b]pyridazin-3-yl)pyrimidine | 0.88(d, 3H), 3.05–3.12(m, 2H), 3.20–3.38 (m, 1H), 4.60(s, 1H), 7.24(d, 1H), 7.44(dd, 1H), 7.77(d, 2H), 8.04–8.08(m, 3H), 8.35(d, 1H), 8.64(s, 1H), 8.68(d, 1H), 8.80(d, 1H), 10.11(s, 1H) | |
| 49 | 2-{4-[N-(1-Methoxyprop-2-yl)sulphamoyl]anilino}-4-(imidazo[1,2b]pyridazin-3-yl)pyrimidine | 0.90(d, 3H), 3.05–3.15(m, 1H), 3.15(s, 3H), 3.23–3.25(m, 2H), 7.40(d, 1H), 7.45(dd, 1H), 7.78(d, 2H), 8.04–8.09(m, 3H), 8.35(d, 1H), 8.64(s, 1H), 8.70(d, 1H), 8.80(d, 1H), 10.15(s, 1H) | |
| 50 | 2-{4-[N-(2-Methylprop-2-yl)sulphamoyl]anilino}-4-(imidazo[1,2b]pyridazin-3-yl)pyrimidine | 1.09(s, 9H), 7.22(s, 1H), 7.44(dd, 1H), 7.78 (d, 2H), 8.03(s, 1H), 8.08(d, 2H), 8.34(d, 1H), 8.64(s, 1H), 8.70(d, 1H), 8.80(d, 1H), 10.09(s, 1H) | 422 [MH]$^+$ |
| 51 | 2-{4-[N-(2-Dimethylaminoethyl)sulphamoyl]anilino}-4-(imidazo[1,2b]pyridazin-3-yl)pyrimidine | 2.08(s, 6H), 2.28(t, 2H), 2.82(t, 2H), 7.24 (s, 1H), 7.42(dd, 1H), 7.79(d, 2H), 8.06(s, 1H), 8.10(d, 2H), 8.35(d, 1H), 8.64(s, 1H), 8.70(d, 1H), 8.80(d, 1H), 10.11(s, 1H) | 439 [MH]$^+$ |
| 52 | 2-[4-(N-cyclobutylsulphamoyl)anilino]-4-(imidazo[1,2b]pyridazin-3-yl)pyrimidine | 1.42–1.50(m, 2H), 1.75(q, 2H), 1.88–1.95 (m, 2H), 3.56–3.64(m, 1H), 7.45(dd, 1H), 7.66–7.78(m, 3H), 8.02–8.08(m, 3H), 8.35 (d, 1H), 8.64(s, 1H), 8.70(d, 1H), 8.80(d, 1H), 10.11(s, 1H) | 422 [MH]$^+$ |
| 53 | 2-{4-[N-(1,3-Dihydroxy-2-methylprop-2-yl)sulphamoyl]anilino}-4-(imidazo[1,2b]pyridazin-3-yl)pyrimidine | 0.98(s, 3H), 3.25–3.31(m, 4H), 4.52(t, 2H), 6.72(s, 1H), 7.45(dd, 1H), 7.80(d, 2H), 8.02–8.10(m, 3H), 8.35(d, 1H), 8.64(s, 1H), 8.70(d, 1H), 8.80(d, 1H), 10.10(s, 1H) | 456 [MH]$^+$ |
| 54 | 2-[4-(N-cyclopropylmethylsulphamoyl)anilino]-4-(imidazo[1,2b]pyridazin-3-yl)pyrimidine | 0.01–0.08(m, 2H); 0.26–0.30(m, 2H), 0.70–0.79 (m, 1H), 2.59(t, 2H), 7.40(d, 1H), 7.72 (d, 2H), 8.0(s, 1H), 8.02(d, 2H), 8.30(d, 1H), 8.60(s, 2H), 8.64(d, 1H), 8.78(d, 1H), 10.05(s, 1H) | 422 [MH]$^+$ |
| 55 | 2-[4-(N-cyclopropylsulphamoyl)anilino]-4- | 0.01–0.08(m, 2H), 0.10–0.15(m, 2H), 1.72–1.78 (m, 1H), 7.10(dd, 1H), 7.30(s, 1H), | 408 [MH]$^+$ |

-continued

| Ex | Compound | NMR | M/z |
|---|---|---|---|
| | (imidazo[1,2b]pyridazin-3-yl)pyrimidine | 7.40(d, 1H), 7.70–7.78(m, 3H), 8.0(d, 1H), 8.33(s, 1H), 8.35(d, 1H), 8.46(d, 1H), 9.8 (s, 1H) | |
| 56 | 2-{4-[N-(2-Methoxyethyl)-N-methylsulphamoyl]anilino}-4-(imidazol[1,2b]pyridazin-3-yl)pyrimidine | 2.71(s, 3H), 3.10(t, 2H), 3.22(s, 3H), 3.42 (t, 2H), 7.42(dd, 2H), 7.75(d, 2H), 8.08(d, 1H), 8.12(d, 2H), 8.32(d, 1H), 8.68(s, 1H), 8.70(d, 1H), 8.80(d, 1H), 10.18(s, 1H) | 440 [MH]$^+$ |
| 57 | 2-{4-[N-(1-Hydroxy-2-methylprop-2-yl)sulphamoyl]anilino}-4-(imidazo[1,2b]pyridazin-3-yl)pyrimidine | 1.2(s, 6H), 3.20(d, 2H), 4.75(t, 1H), 7.09(s, 1H), 7.49(dd, 1H), 7.82(d, 2H), 8.05(d, 2H), 8.09(d, 1H), 8.38(d, 1H), 8.68(s, 1H), 8.70 (d, 1H), 8.85(d, 1H), 10.15(s, 1H) | 440 [MH]$^+$ |

Example 58
2-{4-[N-(1-Methoxy-2-methylprop-2-yl)sulphamoyl] anilino}-4-(imidazo[1,2b]pyridazin-3-yl)pyrimidine Sodium methoxide (96 g 1.8 mmol) was added to 2-{4 [N-(2,2-dimethylaziridyl) sulphonyl]anilino}4-(imidazo[1, 2b]pyridazin-3-yl)pyrimidine (Method 46; 150 mg, 0.36 mmol) in methanol (5 ml) and the mixture heated at 50° C. for 1.5 hours. The solvent was removed by evaporation, the residue dissolved in ethyl acetate/methanol, washed with water, dried (MgSO$_4$) and the solvent removed by evaporation. The crude product was purified by reverse phase chromatography to give the title compound (19 mg, 12%). NMR: 1.12 (s, 6H), 1.88 (m, 2H), 3.15 (s, 3H), 7.42 (d, 1H), 7.77 (dd, 2H), 8.0–8.05 (m, 3H), 8.27 (d, 1H), 6.25 (s, 1H), 8.64 (d, 1H), 8.74 (d,1H); m/z: 454 [MH]$^+$.

Example 59
2-{4-[N-(2-Methoxy-2-methylprop-1-yl)sulphamoyl] anilino}-4-(imidazo[1,2b]pyridazin-3-yl)pyrimidine The second fraction from chromatographic purification described in Example 58 gave the title compound (10 mg, 7%). NMR: 1.09 (s, 6H), 2.65 (d, 2H), 3.05 (s, 3H), 7.25 (t, 1H), 7.46 (dd, 1H), 7.78 (d, 2H), 8.05–8.10 (m, 3H), 8.30 (d, 1H), 8.64 (s, 1H), 8.68 (d,1H), 8.80 (d, 1H), 10.1 (s, 1H); m/z: 454 [MH]$^+$.

Example 60
2-{4-[N-(1-(Pyrolidin-1yl)-2-methylprop-2-yl)sulphamoyl] anilino}-4-(imidazo[1,2b]pyridazin-3-yl)pyrimidine 2-{4-[N-(2,2-Dimethylaziridyl)sulphonyl]anilino}-4-(imidazo[1,2b]pyridazin-3-yl)pyrimidine (Method 46; 150 mg, 0.35 mmol) in pyrrolidine (4 ml) was stirred and heated at 50° C. for 2 hours and then at, ambient temperature for 65 hours. The volatiles were evaporated and the residue dissolved in ethyl acetate/methanol, washed with water and dried (Na$_2$SO$_4$). The solvent was removed by evaporation and the residue triturated with ether to give the title compound (96 mg, 55%). NMR: 1.05 (s, 6H), 1.58–1.63 (m, 4H), 2.43 (s, 2H), 2.53–2.58 (m, 4H), 6.96 (s, 1H), 7.44 (dd, 1H), 7.79 (d, 2H), 8.05 (d, 2H), 8.07 (d, 1H), 8.36 (d, 1H), 8.64 (s, 1H), 8.69 (d, 1H), 8.80 (d, 1H), 10.08 (s, 1H); m/z: 493 [MH]$^+$.

Example 61
2-{4-[N-(1-Methylthio-2-methylprop-2-yl)sulphamoyl] anilino}-4-(imidazo[1,2b]pyridazin-3-yl)pyrimidine A mixture of 2-{4-[N-(2,2-dimethylaziridyl)sulphonyl] anilino}-4-(imidazo[1,2b]pyridazin-3-yl)pyrimidine (Method 46; 150 mg, 0.36 mmol) and sodium methanethiolate (125 mg, 1.8 mmol) in DMF (4 ml) was heated at 80° C. for 18 hours. The solvent was removed by evaporation, the residue dissolved in ethyl acetate/methanol, washed with water, dried (MgSO$_4$) the solvent evaporated. The residue was triturated with ether to give the title compound (90 mg, 54%). NMR: 1.15 (s, 6H), 2.10 (s, 3H), 2.65 (s, 2H), 7.40 (s, 1H), 7.50 (dd, 1H), 7.82 (d, 2H), 8.08–8.1 (m, 3H), 8.39 (d, 1H), 8.69 (s, 1H), 8.73 (d, 1H), 8.80 (d, 1H), 10.15 (s,1H); m/z: 470 [MH]$^+$.

Example 62
2-{4-[N-(1-Morpholino-2-methylprop-2-yl)sulphamoyl] anilino}-4-(imidazo[1,2b]pyridazin-3-yl)pyrimidine 2-{4-[N-(2,2-Dimethylaziridyl)sulphonyl]anilino}-4-(imidazo[1,2b]pyridazin-3-yl)pyrimidine (120 mg, 0.29 mmol) in morpholine (5 ml) was heated reflux 3 hours. The solvent was evaporated, the residue was dissolved in ethyl acetate/methanol, washed with water, dried (MgSO$_4$) and the solvent evaporated. The residue was triturated with ether to give the title compound (50 mg, 35%). NMR: 1.05 (s, 6H), 2.29 (s, 2H), 2.43–2.50 (m, 4H), 3.48–3.52 (m, 4H), 7.04 (s, 1H), 7.43 (dd, 1H), 7.78 (d, 2M), 8.02–8.08 (m, 3H), 8.35 (d, 1H), 8.64 (s, 1H), 8.71 (d, 1H), 8.80 (d, 1H), 10.08 (s, 1H).

Example 63
2-{4-[N-(1,3-Dimethoxyprop-2-yl)sulphamoyl]anilino}-4-(imidazo[1,2b]pyridazin-3-yl)pyrimidine Chlorosulphonic acid (0.23 ml, 3.3 mmol) was added to a solution of 2-anilino-4-(imidazo[1,2b]pyridazin-3-yl) pyrimidine (Example 10; 300 mg, 1.04 mmol) in thionyl chloride (6 ml) at 5° C. The mixture was stirred at 5° C. for 30 minutes, then at ambient temperature for 1 hour and finally heated at reflux for 1.5 hour. The mixture was allowed to cool to ambient temperature and a solution of 1,3-dimethoxy-2-aminopropane (Method 57; 14 mmol) in ethanol (20 ml) and dimethylethylamine (1 ml) were added to the residue, and the mixture stirred at ambient temperature for 18 hours. The volatiles were removed by evaporation, the residue triturated with water and the solid product collected by filtration and then dried under vacuum at 60° C. to give the title compound (322 mg, 66%). NMR: 3.10 (s, 6H), 3.21 (d, 4H), 7.42–7.58 (m, 2H), 7.78 (d, 2H), 8.02–8.08 (m, 3H), 8.35 (d, 1H), 8.65–8.70 (m, 2H), 8.80 (d, 1H), 10.09 (s, 1H); m/z: 470 [MH]$^+$.

Examples 64–66

The following compounds were prepared by a method analogous to that described in Example 63.

| Ex | Compound | NMR | M/z |
|---|---|---|---|
| 64[1] | 2-{4-[N-(1-Ethoxyprop-2-yl)sulphamoyl]anilino}-4-(imidazo[1,2b]pyridazin-3-yl)pyrimidine | 0.90(d, 3H), 1.05(t, 3H), 3.08–3.12(m, 1H), 3.22–3.30(m, 4H), 7.39(d, 2H), 7.45(dd, 1H), 7.79(d, 2H), 8.03–8.09(m, 3H), 3.35(d, 1H), 8.64(s, 1H), 8.70(d, 1H), 8.80(d, 1H) | 454 [MH]+ |
| 65[2] | 2-{4-[N-(1-Propoxyprop-2-yl)sulphamoyl]anilino}-4-(imidazo[1,2b]pyridazin-3-yl)pyrimidine | 0.79(t, 3H), 0.94(d, 3H), 1.40(q, 2H), 3.08–3.12 (m, 1H), 3.18–3.20(m, 2H), 7.38(d, 1H), 7.43(dd, 1H), 7.78(d, 2H), 8.03–8.09(m, 3H), 8.36(d, 1H), 8.62(s, 1H), 8.68(d, 1H), 8.81(d, 1H), 10.11(s, 1H) | 468 [MH]+ |
| 66[3] | 2-{4-[N-(1,3-Diethoxyprop-2-yl)sulphamoyl]anilino}-4-(imidazo[1,2b]pyridazin-3-yl)pyrimidine | 0.99(t, 6H), 3.23–3.31(m, 9H), 7.42–7.51(m, 2H), 7.78(d, 2H), 8.02–8.09(m, 3H), 8.34(d, 1H), 8.62(s, 1H), 8.70(d, 1H), 8.80(d, 1H), 10.08(s, 1H) | 498 [MH]+ |

[1] 1-Ethoxy-2-aminopropane (Method 54) as starting material, purified by chromatography eluting with dichloromethane/isohexane (1:1) increasing in polarity to dichloromethane/methanol (97:3)
[2] 1-Propoxy-2-aminopropane (Method 55) as starting material, purified by chromatography on silica gel eluting with dichloromethane/methanol (100:0) increasing in polarity to (95:5).
[3] 1,3-Diethoxy-2-aminopropane (Method 56) as starting material, purified by chromatography on silica gel eluting with dichloromethane/isohexane (1:1) increasing in polarity to dichloromethane/methanol (98.5:1.5)

Preparation of Starting Materials

The starting materials for the Examples above are either commercially available or are readily prepared by standard methods from known materials. For example the following reactions are illustrations but not imitations of the preparation of some of the starting materials used in the above reactions.

Method 1
3-(1-Hydroxyethyl)imidazo[1,2a]pyrazine

Anhydrous neutral alumina (activity 1) (28.5 g) was added to a stirred solution of 2-aminopyrazine (2.85 g, 30 mmol) in dry dichloromethane (100 ml) under nitrogen. A solution of 2,3-epoxybutanal (5.58 g, 30 mmol) in dichloromethane (10 ml) was added and the reaction mixture stirred for 18 hours. The reaction mixture was filtered, and the alumina cake washed with dichloromethane (100 ml), and methanol/dichloromethane (1:1, 100 ml). The filtrates were combined, the volatiles were removed by evaporation (keeping the bath temperature below 40° C.). The resulting crude yellow oil was triturated with dichloromethane and the solid collected by filtration to give the title compound (586 mg, 12%) as a pale orange solid. NMR: 1.6 (d, 3H), 5.18 (quin, 1H), 5.5 (d, 1H), 7.7 (s, 1H), 7.88 (d,1H), 8.5 (d, 1H), 9.0 (s, 1H).

Method 2
3-Acetylimidazo[1,2a]pyrazine 3-(1-Hydroxyethyl)imidazo[1,2a]pyrazine (Method 1; 3.87 g, 23.7 mmol) was dissolved in acetone (30 ml) with manganese dioxide (21.1 g, 237 mmol) and stirred at ambient temperature for 72 hours. The solution was filtered through diatomaceous earth, washed with acetone (4×50 ml) and then with methanol (3×50 ml). The solvent was removed from the filtrate by evaporation. The residue was purified by column chromatography eluting with methanol/dichloromethane (0:100 increasing in polarity to 10:90) to give the title compound (349 mg, 10%) as a pure crystalline white solid. NMR: 2.60 (s, 1H), 8.22 (d, 1H), 8.75 (s, 1H), 9.35 (m, 2H).

Method 3
3-(3-Dimethylaminoprop-2-en-1-oyl)imidazo[1,2a]pyrazine

A mixture of 3-acetylimidazo[1,2a]pyrazine (Method 2; 340 mg, 2.11 mmol) and DMFDMA (20 ml) were heated under reflux, under nitrogen for 18 hours. The mixture was allowed to cool and the solvent removed by evaporation. The residue was triturated with ether, collected by filtration and dried to give the title compound (406 mg, 89%) as a dark red solid. NMR: 2.91 (br s, 3H) 3.15 (br s, 3H), 5.4 (d, 1H), 7.75 (d, 1H), 8.18 (d, 1H), 8.6 (s, 1H), 9.19 (s,1H), 9.55 (dd, 1H)); m/z: 218 [MH]+.

Method 4
2-[4-Sulphonoylanilino]-4-(imidazo[1,2a]pyrazin-3-yl)pyrimidine

2-Anilino-4-(imidazo[1,2a]pyrazin-3-yl)pyrimidine (Example 9; 350 mg, 1.22 mmol) was added in portions to concentrated sulphuric acid (6 ml) stirred and cooled with an ice-bath to maintain temperature <25° C. The reaction mixture was allowed to warm to ambient temperature and stirred for 1 hour. The mixture was then carefully poured into ice-water (150 ml) and the ice allowed to melt. The sodium hydroxide pellets and then 1M aqueous sodium hydroxide solution was carefully added to adjusted the solution from pH0.5 to pH2. The mixture was stirred at ambient temperature for 18 hours and the resulting precipitate collected by filtration, washed with water (2×15 ml) and dried. The crude product was triturated with dichloromethane then recollected by filtration and then was re-triturated with dichloromethane/methanol (1:1) recollected by filtration and dried to give the title compound (191 mg, 52%). NMR: 7.54 (d, 1H), 7.60 (d, 2H), 7.64 (d, 2H), 8.15 (d, 1H), 8.54 (d, 1H), 8.81 (s, 1H), 9.95 (br s, 1H); m/z: 367 [M−H]−.

Method 5
3-(1-Hydroxyethyl)imidazo[1,2a]pyrimidine

2-Aminopyrimidine (2.85 g, 30 mmol) was treated by the method described in Method 1 to give crude product which was purified by column chromatography on neutral alumina (activity 3) eluting with dichloromethane/methanol (100:0 increasing in polarity to 95:5) to give the title compound (662 mg, 14%). NMR: 1.59 (d, 3H), 5.12 (quin, 1H), 5.39 (d, 1H), 7.15 (dd, 1H), 7.60 (s, 1H), 8.53 (dd, 1H), 8.96 (dd, 1H); m/z: 164 [MH]$^+$.

Method 6

3-Acetylimidazo[1,2a]pyrimidine 3-(1-Hydroxyethyl)imidazo[1,2a]pyrimidine (Method 5; 630 mg, 3.87 mmol) was treated with manganese dioxide (3.44 g, 38.7 mmol) as described in Method 2 but without chromatographic purification to give the title compound (379 mg, 60%) as a pale yellow solid. NMR: 2.56 (s, 3H), 7.29 (t, 1H), 8.76 (s, 1H), 8.80 (m, 1H), 9.78 (dd, 1H).

Method 7

3-(3-Dimethylaminoprop-2-en-1-oyl)imidazo[1,2a]pyrimidine.

3-Acetylimidazo[1,2a]pyrimidine (Method 6; 370 mg, 2.29 mmol) was treated as described in Method 3 to give the title compound (479 mg, 96%). NMR: 2.94 (br s, 1H), 3.15 (br s, 3H), 5.83 (d, 1H), 7.22 (dd, 1H), 7.70 (s, 1H), 8.60 (s, 1H), 8.68 (dd, 1H), 8.96 (dd, 1H); m/z: 217 [MH]$^+$.

Method 8

2-[4-Sulphonoylanilino]-4-(imidazo[1,2a]pyrimidin-3-yl)pyrimidine

2-Anilino-4-(imidazo[1,2a]pyrimidin-3-yl)pyrimidine (70% isomeric mixture with 2-anilino-4-(imidazo[1,2a]pyrimidin-2-yl)pyrimidine) (Example 11; 392 mg, 1.36 mmol) was treated as described in Method 4 to give the title compound as the major component (70%) in an isomeric mixture with 2-[4-sulphonoylanilino]-4-(imidazo[1,2a]pyrimidin-2-yl)pyrimidine (363 mg, 73%). NMR: 7.47 (d, 1H), 7.45–7.7 (m, 5H), 8.57 (d, 1H), 8.93 (dd, 1H), 9.02 (s, 1H), 9.82 (s, 1H), 10.4 (d, 1H).

Method 9

5-Chloroimidazo[1,2b]pyridazine

A mixture of 3-amino-6-chloropyridazine (5.0 g, 38.6 mmol) and chloroacetaldehyde (5.9 ml of a 7.9M solution in water, 46.3 mM) in 1-butanol (37 ml) was heated at 120° C. with for 20 hours. The reaction was allowed to cool to ambient temperature and the crystallised solid collected by filtration, washed with a little 1-butanol and then ether. The solid was dissolved in water (50 ml) and the solution adjusted to pH10 by carefully addition of 40% aqueous sodium hydroxide solution. The resulting suspension was extracted with ethyl acetate. The organic extracts were combined, washed with saturated brine, dried (Na$_2$SO$_4$) and the volatiles were removed by evaporation. The residue was triturated with isohexane, collected by filtration, washed with isohexane and dried to give the title compound (4.35 g, 74%) as a pale brown solid. NMR: 7.33 (d, 1H), 7.83 (s, 1H), 8.20 (d, 1H), 8.32 (s, 1H); m/z: 154 [MH]$^+$.

Method 10

Imidazo[1,2b]pyridazine

A mixture of 5-chloroimidazo[1,2b]pyridazine (Method 9; 5.82 g, 37.9 mmol), triethylamine (5.28 ml, 37.9 mmol) and 5% palladium on charcoal (300 mg) in ethyl acetate (233 ml) was stirred vigorously under an atmosphere of hydrogen until the uptake of hydrogen ceased. The reaction mixture was filtered through diatomaceous earth. The filter pad was washed with ethyl acetate and volatiles removed from the filtrate by evaporation. The residue was triturated with ice cold pentane, collected by filtration, washed sparingly with cold pentane and dried to give the title compound (3.65 g, 81%) as a white solid. NMR (CDCl$_3$): 7.03 (dd, 1H), 7.78. (s, 1H), 7.95 (m, 2H), 8.30 (d, 1H); m/z: 120 [MH]$^+$.

Method 11

3-Bromoimidazo[1,2b]pyridazine

N-Bromosuccinimide (2.7 g, 15.1 mmol) was added to a solution of imidazo[1,2b]pyridazine (Method 10; 1.8 g, 15.1 mmol) in chloroform (15 ml) and the mixture was stirred and heated at reflux for 20 minutes. The reaction mixture was allowed to cool to ambient temperature and saturated aqueous sodium carbonate solution (15 ml) was added and the mixture stirred vigorously. More chloroform and water was added to dissolved the precipitated solids. The organic layer was separated, dried (Na$_2$SO$_4$) and the solvent removed by evaporation. The residue was recrystallized from ethanol (50 ml), collected by filtration, washed with cold ethanol and dried to give the title compound (2.61 g, 88%) as an off white solid. NMR(CDCl$_{23}$): 7.10 (dd, 1H), 7.80 (s, 1H), 7.95 (d, 1H), 8.47 (d, 1H); m/z: 198 [MH]$^+$.

Methods 12–13

The following compounds were prepared by a method analogous to that described in Method 11, except that they were reacted at ambient temperature for 4 hours.

| Meth | Compound | NMR | M/z | SM |
|---|---|---|---|---|
| 12 | 3-Bromo-5-methoxyimidazo[1,2b]pyridazine | 3.99(s, 3H), 6.94(d, 1H), 7.71(s, 1H), 8.02(d, 1H) | 230 [MH]$^+$ | Meth 41 |
| 13[1] | 3-Bromo-5-(2,2,2-trifluoroethoxy)imidazo[1,2b]pyridazine | 5.08(q, 2H), 7.12(d, H), 7.8(s, H), 8.16(d, 1H) | 298 [MH]$^+$ | Meth 42 |

[1]Re-crystallisated from ethyl acetate/isohexane

Method 14

3-Acetylimidazo[1,2b]pyridazine

Isopropyl magnesium bromide (12.5 ml of a 1M solution in THF, 12.5 mmol) was added dropwise over 5 minutes to a stirred solution of 3-bromoimidazo[1,2b]pyridazine (Method 11; 1.98 g, 10 mmol) in dry THE (100 ml) under nitrogen at −40° C. The reaction mixture was stirred for 105 minutes at −40° C. and then dry N-methoxy-N-methylacetamide (1.65 ml, 16 mmol) was added. The mixture was stirred a further 30 minutes at −40° C. and then allowed to warm to ambient temperature and stirred for a further 90 minutes. Acetic Acid (1.26 ml) was added and the volatiles then removed by evaporation. The residue was partitioned between dichloromethane (120 ml) and water (30 ml). The layers were separated and the aqueous layer was extracted with dichloromethane. The organic layers were combined, dried (Na$_2$SO$_4$) and volatiles removed by evaporation. The residue was triturated with ether and isohexane, collected by filtration, washed with isohexane and dried to give the title compound (1.25 g, 78%) as a brown solid. NMR (CDCl$_3$): 2.75 (s, 3H), 7.27 (dd, 1H), 8.08 (d, 1H), 8.45 (s, 1H), 8.62 (d, 1H); m/z: 162 [MH]$^+$.

Methods 15–16

The following compounds were prepared by a method analogous to that described in Method 14.

| Meth | Compound | NMR | M/z | SM |
|---|---|---|---|---|
| 15[1] | 3-Acetyl-5-methoxyimidazo[1,2b]pyridazine | 2.64(s, 3H), 4.0(s, 3H), 7.15(d, 1H), 8.17(d, 1H), 8.3(s, 1H) | 192 [MH]$^+$ | Meth 12 |
| 16[2] | 3-Acetyl-5-(2,2,2-trifluoroethoxy)imidazo[1,2b]pyridazine | 2.65(s, 3H), 5.10(q, 2H), 7.30(d, 1H), 8.27(d, 1H), 8.37(s, 1H) | | Meth 13 |

[1] Re-crystallisated from ethyl acetate/isohexane
[2] 1:1 mix of product and 5-(2,2,2-trifluoroethoxy)imidazo[1,2b]pyridazine Method 17
3-(3-Dimethylaminoprop-2-en-1-oyl)imidazo[1,2b]pyridazine 3-Acetylimidazo[1,2b]pyridazine (Method 14; 1.25 g, 7.76 mmol) was suspended in DMFDMA (32 ml) and the mixture heated under nitrogen at 100° C. for 42 hours. The excess dimethylacetal was removed by evaporation and the residue triturated with ether and isohexane. The product was collected by filtration, washed with isohexane and dried to give the title compound (1.58 g, 94%) as a brown solid. NMR (CDCl$_{23}$): 3.00 (s, 3H), 3.17 (s, 3H), 6.20 (d, 1H), 7.13 (dd, 1H), 7.92 (d,1H), 8.03 (d, 1H), 8.38 (s, 1H), 8.50 (d, 1H); m/z: 217 [MH]$^+$.

Methods 18–24

The following compounds were prepared by a method analogous to that described in Method 17.

Method 25
2-Fluorophenylguanidine Bicarbonate

Concentrated hydrochloric acid (6 ml) in water (4.8 ml) was added to a mixture of 2-fluoroaniline (7.94 g, 71.2 mmol) and cyanamide (6.98 g, 166 mmol) and the mixture heated at 115° C. for 2.5 hours. The reaction mixture was allowed to cool to ambient temperature and the solution was adjusted to pH 13 by careful addition of 40% aqueous sodium hydroxide solution. The aqueous solution was extracted with ethyl acetate and the combined organic extracts were dried (Na$_2$SO$_4$) and the volatiles removed by evaporation. The crude product was dissolved in water (40 ml) and carbon dioxide gas bubbled through the solution until the pH of the suspension remained constant (approximately pH 9). The precipitated solid was collected by filtration, washed sparingly with water and dried to give the title compound (11.95 g, 78%) as a white solid. NMR: 6.83 (m, 2H), 7.0 (m, 2H; m/z: 154 [MH]$^+$.

| Meth | Compound | NMR | M/z | SM |
|---|---|---|---|---|
| 18 | 3-(3-Dimethylaminoprop-2-en-1-oyl)-2-methylimidazo[1,2b]pyridazine | 2.58(s, 3H), 2.87(s, 3H), 2.9(s, 3H), 6.27(d, 1H), 7.27(dd, 1H), 7.73(d, 1H), 8.05(d, 1H), 8.56(d, 1H) | 231 [MH]$^+$ | Meth 34 |
| 19 | 3-(3-Dimethylaminoprop-2-en-1-oyl)-2-ethylimidazo[1,2b]pyridazine | 1.23(t, 3H), 2.87(s, 3H), 3.0(q, 2H), 3.13(s, 3H), 6.23(d, 1H), 7.25 (dd, 1H), 7.70(d, 1H), 8.07(d, 1H), 8.56(d, 1H) | 245 [MH]$^+$ | Meth 35 |
| 20 | 3-(3-Dimethylaminoprop-2-en-1-oyl)-5-methoxy imidazo[1,2b]pyridazine | 2.9(br s, 3H), 3.15(br s, 3H), 4.02 (s, 3H), 6.43(d, 1H), 7.0(d, 1H), 7.8(d, 1H), 8.03(s, 1H), 8.05(d, 1H) | 247 [MH]$^+$ | Meth 15 |
| 21 | 3-(3-Dimethylaminoprop-2-en-1-oyl)-5-(2,2,2-trifluoroethoxy)imidazo[1,2b]pyridazine | 2.94(br s, 3H), 3.18(br s, 3H), 5.16 (q, 2H), 6.3(d, 1H), 7.18(d, 1H), 7.8(d, 1H), 8.14(s, 1H), 8.2(d, 1H) | 315 [MH]$^+$ | Meth 16 |
| 22 | 3-(3-Dimethylaminoprop-2-en-1-oyl)-6,7-dimethyl imidazo[1,2b]pyridazine | 2.35(s, 3H), 2.50(s, 3H), 2.95(br s, 3H), 3.15(br s, 3H), 6.25(d, 1H), 7.75(d, 1H), 8.20(s, 1H), 8.50(s, 1H) | 245 [MH]$^+$ | Meth 37 |
| 23 | 3-(3-Dimethylaminoprop-2-en-1-oyl)-6-methylimidazo[1,2b]pyridazine | 2.4(s, 3H), 2.90(br s, 3H), 3.15(br s, 3H), 6.2(d, 1H), 7.74(d, 1H), 7.97(s, 1H), 8.19(s, 1H), 8.56(s, 1H) | 231 [MH]$^+$ | Meth 38 |
| 24[1] | 3-(3-Dimethylaminoprop-2-en-1-oyl)-2-dimethylamino imidazo[1,2b]pyridazine | 2.96(s, 12H), 5.9(d, 1H), 7.13(dd, 1H), 7.53(d, 1H), 7.8(d, 1H), 8.33 (d, 1H) | 260 [MH]$^+$ | Meth 36 |

[1] By a similar method, but heating at 100° C. for 120 hours and purifying the product by chromatography eluting with dichloromethane/methanol (95:5)

Method 26

N,N-Dimethyl-N'-(6-chloropyridazin-3-yl)acetamidine

3-Amino-6-chloropyridazine (1.29 g, 10 mmol) was suspended in dry toluene (20 ml) and dimethylacetamide dimethyl acetal (1.46 ml, 10 mmol) was added. The mixture was stirred and heated at reflux for 3 hours and then left to stand at ambient temperature for 18 hours. Insolubles were removed from the reaction mixture by filtration and the filter washed with ethyl acetate. The filtrate was then evaporated and the residue triturated with isohexane, the solid product collected by filtration and washed with isohexane to give the title compound (1.7 g, 85%) as a yellow solid. NMR: ($CDCl_3$) 2.13 (s, 3H), 3.1 (s, 6H), 6.92 (d, 1H), 7.25 (d, 1H); m/z: 199 $[MH]^+$.

Methods 27–28

The following compounds were prepared by a method analogous to that described in Method 26.

Method 34

3-Acetyl-2-methylimidazo[1,2b]pyridazine

A mixture of 3-acetyl-5-chloro-2-methylimidazo[1,2b] pyridazine (Method 29; 4.8 g, 22.9 mmol), triethylamine (3.21 ml, 22.9 mmol) and 5% palladium on charcoal (1.6 g) in ethyl acetate (180 ml) was stirred vigorously under an atmosphere of hydrogen until the uptake of hydrogen ceased. The reaction mixture was filtered through diatomaceous earth. The filter pad was washed with ethyl acetate and volatiles removed from the filtrate by evaporation. The residue was triturated with isohexane, collected by filtration, washed sparingly with isohexane and dried to give the title compound (3.7 g, 92%) as a white solid. NMR: 2.6 (s, 3H), 2.73 (s, 3H), 7.43 (dd, 1H), 8.15 (d, 1H), 8.67 (d, 1H); m/z: 176 $[MH]^+$.

| Meth | Compound | NMR | M/z | SM |
|---|---|---|---|---|
| 27[1] | N,N-Dimethyl-N'-(6-chloro-4,5-dimethylpyridazin-3-yl)acetamidine | 2.22(s, 3H), 2.24(s, 3H), 3.02(s, 3H), 3.1(s, 3H), 8.38(s, 1H) | 213 $[MH]^+$ | Com av |
| 28[2] | N,N-Dimethyl-N'-(6-chloro-5-methylpyridazin-3-yl)acetamidine | 2.24(s, 3H), 3.0(s, 3H), 3.12(s, 3H), 7.1(s, 1H), 8.45(s, 1H) | 199 $[MH]^+$ | Meth 43 |

[1]Heating at 120° C. for 7 hours
[2]Purified by column chromatography eluting with isohexane/ethyl acetate (70:30 increasing in polarity to 90:10):-

Method 29

3-Acetyl-5-chloro-2-methylimidazo[1,2b]pyridazine

Chloroacetone (2.9 ml, 36.2 mmol) was added to a suspension of powdered sodium bromide (3.73 g, 36.2 mmol) in ethanol (75 ml) and the mixture stirred at ambient temperature for 2 hours. N,N-dimethyl-N'-(6-chloropyridazin-3-yl)acetamidine (Method 26; 6.0 g, 30.2 mmol) was added and the suspension stirred and heated at reflux for 5.5 hours. The reaction mixture was allowed to cool to ambient temperature and the volatiles removed by evaporation. Water (60 ml) was added to the residue and the resulting precipitate collected by filtration, washed with water and dried to give the title compound (4.93 g, 79%) as a pale yellow solid. NMR: 2.6 (s, 3H), 2.7 (s, 3H), 7.57 (d, 1H), 8.23 (d, 1H); m/z: 209 $[MH]^+$.

Methods 30–33

The following compounds were prepared by a method analogous to that described in Method 29.

| Meth | Compound | NMR | M/z | SM |
|---|---|---|---|---|
| 30 | 3-Acetyl-5-chloro-2-ethylimidazo[1,2b]pyridazine | 1.23 (t, 3H), 2.7 (s, 3H), 3.02 (q, 2H), 7.58 (d, 1H), 8.25 (d, 1H) | 224 $[MH]^+$ | Meth 39 |
| 31[1] | 3-Acetyl-5-chloro-2-dimethylaminoimidazo[1,2b]pyridazine | ($CDCl_3$): 2.78 (s, 3H), 3.13 (s, 6H), 7.13 (d, 1H), 7.63 (d, 1H) | 239 $[MH]^+$ | Meth 40 |
| 32[2] | 3-Acetyl-5-chloro-6,7-dimethylimidazo[1,2b]pyridazine | 2.4 (s, 3H), 2.62 (s, 3H), 2.65 (s, 3H), 8.50 (s, 1H) | 224 $[MH]^+$ | Meth 27 |
| 33[3] | 3-Acetyl-5-chloro-6-methylimidazo[1,2b]pyridazine | 2.45 (s, 3H), 2.6 (s, 3H), 8.32 (s, 1H), 8.52 (s, 1H) | 210 $[MH]^+$ | Meth 28 |

[1]Using acetonitrile as the reaction solvent and heating at 65° C. for 24 hours:-
[2]Using DMF as the reaction solvent and heating at 70° C. for 12 hours followed by purification of the product by passing through an SCX ion exchange column eluting with 2N methanolic ammonia/dichloromethane (50:50) and recrystalisation from ethyl acetate/methanol
[3]Using DMF as the reaction solvent and sodium iodide in place of sodium bromide and heating at 70° C. for 12 hours Methods 35–38

The following compounds were prepared by a method analogous to that described in Method 34.

| Meth | Compound | NMR | M/z | SM |
|---|---|---|---|---|
| 35 | 3-Acetyl-2-ethyl imidazo[1,2b]pyridazine | 1.23 (t, 3H), 2.73 (s, 3H), 3.02 (q, 2H), 7.43 (dd, 1H), 8.18 (d, 1H), 8.68 (d, 1H) | 190 [MH]$^+$ | Meth 30 |
| 36 | 3-Acetyl-2-dimethylamino imidazo[1,2b]pyridazine | 2.67 (s, 3H), 3.0 (s, 6H), 7.35 (dd, 1H), 7.93 (d, 1H), 8.5 (d, 1H) | 205 [MH]$^+$ | Meth 31 |
| 37 | 3-Acetyl-6,7-dimethyl imidazo[1,2b]pyridazine | 2.39 (s, 3H), 2.55 (s, 3H), 2.65 (s, 3H), 8.45 (s, 1H), 8.78 (s, 1H) | 190 [MH]$^+$ | Meth 32 |
| 38[1] | 3-Acetyl-6-methyl imidazo[1,2b]pyridazine | 2.44 (s, 3H), 2.62 (s, 3H), 8.07 (q, 1H), 8.44 (s, 1H), 8.64 (d, 1H) | 176 [MH]$^+$ | Meth 33 |

[1]Using ethanol as the reaction solvent

Method 39

N,N-Dimethyl-N'-(6-chloropyridazin-3-yl)propionamidine

A solution of phosphorous oxytrichloride (9.32 ml, 100 mmol) in dry toluene (30 ml) was added dropwise over 15 minutes to a stirred solution of dimethyl propionamide (10.88 ml, 100 mmol) in dry toluene (180 ml) and the mixture was then stirred for 24 hours at ambient temperature. 3-Amino-6-chloropyridazine (12.9 g, 100 mmol) was added as a solid and the mixture stirred and heated at 85° C. for 18 hours. The reaction mixture was allowed to cool and settle and the toluene layer decanted off. The residue was washed with more dry toluene and this decanted off. The residue was dissolved in water and extracted with dichloromethane and the aqueous layer was adjusted to pH 12 by careful addition of 40% aqueous sodium hydroxide solution. Dichloromethane was added and the mixture was filtered to remove the insoluble impurity. The organic layer was separated and the aqueous layer extracted with dichloromethane. The organic extracts were combined, dried Na$_2$SO$_4$) and the volatiles removed by evaporation. The crude product was purified by column chromatography on silica gel eluting with dichloromethane/methanol (96.5:3.5) to give the title compound (4.4 g, 21%) as a brown oil. NMR (CDCl$_3$): 1.18 (t, 3H), 2.53 (q, 2H), 3.1 (s, 6H), 6.93 (d, 1H), 7.27 (d, 1H); m/z: 213 [MH]$^+$.

Method 40

The following compound was prepared by a method analogous to that described in Method 39.

| Meth | Compound | NMR | M/z |
|---|---|---|---|
| 40 | N,N,N'N'-Tetramethyl-N"-(6-chloropyridazin-3-yl)guanidine | (CDCl$_3$) 3.0 (s, 12H), 7.5 (d, 1H), 7.67 (d, 1H) | 228 [MH]$^+$ |

Method 41

5-Methoxyimidazo[1,2b]pyridazine

Sodium methoxide solution (25% wt solution in methanol, 56.5 g, 261.4 mmol) was added to a solution of 5-chloroimidazo[1,2b]pyridazine (Method 9; 10.0 g, 65.6 mmol) in anhydrous methanol (100 ml) at ambient temperature and the reaction mixture stirred for 18 hours. The volatiles were removed by evaporation and the yellow, oily residue was dissolved in dichloromethane (100 ml). The solution was washed with water (5×100 ml) until aqueous wash became neutral. The organic solution was dried (MgSO$_4$) and the solvent removed to give the title compound (8.87 g, 91%) as a pale yellow solid. NMR: 3.92 (s, 3H), 6.82 (d, 1H), 7.59 (s, 1H), 7.99 (d, 1H), 8.03 (s, 1H); m/z: 150 [MH]$^+$.

Method 42

5-(2,2,2-Trifluoroethoxy)imidazo[1,2b]pyridazine

Sodium hydride (432 mg, 10.8 mmol) was added in portions to a solution of 2,2,2-trifluoroethanol (10.8 mmol) and 5-chloroimidazo[1,2b]pyridazine (1.5 g, 9.8 mmol), in anhydrous DMF (15 ml) at ambient temperature and the mixture stirred for 18 hours. The volatiles were removed by evaporation and the resulting solid was dissolved in dichloromethane (20 ml). The solution was washed with water (2×15 ml), the organic layer dried (MgSO$_4$) and the solvent removed by evaporation to give the title compound (2.05 g, 92%) as a pale yellow solid. NMR: 5.0 (q, 2H), 7.0 (d, 1H), 7.64 (s, 1H), 8.1 (m, 2H); m/z: 219 [MH]$^+$.

Method 43

3-Amino-6-chloro-5-methylpyrazine

A mixture of 3,6-dichloro-5-methylpyrazine (5 g, 30.7 mmol) in ethanolic ammonia solution (50 ml) was heated for 8 hours in a high-pressure cell at 135° C. The solvent was then removed by evaporation and the residue dissolved in chloroform (40 ml). The organic solution was washed with water (2×25 ml) dried (MgSO$_4$) and the volatiles removed by evaporation. The crude solid was semi-purified by column chromatography on silica gel eluting with dichloromethane/methanol (95:5) to the title compound (1.3 g, 31%) as a 10:17 mixture with its regioisomer. NMR: 2.06 (s, 3H), 2.18 (s, 3H), 6.2 (br s, 4H), 6.74 (s, 1H), 7.26 (s, 1H); m/z: 143 [MH]$^+$.

Method 44

1-(2-Aminoethyl)pyrazole

Sodium hydroxide (22.96 g, 0.57 mol) was added to a solution of pyrazole (10.88 g, 0.16 mol) in dry acetonitrile (80 ml) and the mixture stirred at ambient temperature for 30 minutes. Tetrabutylammonium hydrogen sulphate (2.18 g, 6.4 mmol) and 2-chloroethylamine hydrochloride (19.78 g, 0.172 mole) were added and the mixture heated at reflux for 24 hours. The mixture was allowed to cool and the insolubles were removed by filtration. The volatiles were removed from the filtrate by evaporation and 49% hydrogen bromide (30 ml) followed by ethanol (100 ml) added to the residue. The mixture was heated to reflux and then cooled in ice. The resulting precipitate was collected by filtration, washed with cold ethanol to give the title compound. NMR: 3.20–3.24 (m, 2H), 4.38 (t, 2H), 6.30 (s, 1H), 7.50 (s, 1H), 7.79 (s, 1H), 7.98 (s, 2H).

Method 45

2-{4-[N-(1-(4-Toluenesulphonyloxy)-2-methylprop-2-yl)sulphamoyl]anilino}-4-(imidazo[1,2b]pyridazin-3-yl)pyrimidine 4-Toluenesulphonyl chloride (4.44 g, 0.23 mol) was added to a solution of 2-{4-[N-(1-hydroxy-2-methylprop-2-yl)sulphamoyl]anilino}(imidazo[1,2b]pyridazin-3-yl)pyrimidine (Example 57; 3.41 g, 0.008 mol) in pyridine (50 ml) and the mixture stirred at ambient temperature for 24 hours. The mixture was then diluted with water and sonicated. The aqueous phase was decanted and the residue dissolved in ethyl acetate/methanol. The solution was washed with water, dried (MgSO$_4$), the solvent removed by evaporation and the residue was triturated with ether to give the title compound (1.92 g, 42%). NMR: 1.0 (s, 6H), 2.38 (s, 3H), 3.79 (s, 2H), 7.40–7.45 (m, 3H), 7.59 (s, 1H), 7.65–7.75 (m, 4H), 8.05 (d, 2H), 8.09 (d, 1H), 8.35 (d, 1H), 8.66 (s, 1H), 8.70 (d, 1H), 8.80 (d, 1H), 10.13 (s, 1H).

Method 46

2-{4-[N-(2,2-dimethylaziridyl)sulphonyl]anilino}-4-(imidazo[1,2b]pyridazin-3-yl)pyrimidine Potassium carbonate (57 mg, 0.4 mmol) and then acetone (5 ml) was added to 2-{4-[N-(1-(4-toluenesulphonyloxy)-2-methylprop-2-yl)sulphamoyl]anilino}-4-(imidazo[1,2b]pyridazin-3-yl)pyrimidine (Method 45; 220 mg, 0.38 mmol) and the mixture stirred and heated at reflux for 2 hours. The mixture was allowed to cool, the insolubles were removed by filtration, the filter washed with acetone, and the solvent removed by evaporation to give the title compound (123 mg, 77%) as an orange solid. NMR: 1.42 (s, 6H), 2.43 (s, 2H), 7.43 (dd, 1H), 7.84 (d, 2H), 8.08–8.12 (m, 3H), 8.35 (d, 1H), 8.68 (d, 1H), 8.70 (d, 1H), 8.8 (d, 1H), 10.2 (s, 1H).

Method 47

1-(1-Methylcyclopropane)carboxamide

Oxalyl chloride (8.24 ml, 0.095 mol) and then DMF (few drops) were added to a solution of 1-(1-methylcyclopropane)carboxylic acid (9.42 g, 0.094 mol) in dichloromethane (150 ml) cooled at 5° C. and the mixture stirred at 5° C. for 30 minutes and then for 3 hours at ambient temperature. The solvent and excess oxalyl chloride were removed by evaporation, the residue dissolved in dichloromethane and added to a solution of ammonia (excess) in methanol cooled at 5° C. The mixture was allowed to warm to ambient temperature and the volatiles removed by evaporation to give the title compound. NMR: 0.29 (q, 2H), 0.71 (q, 2H), 1.02 (s, 3H), 6.62 (s, 1H), 6.85 (s, 1H).

Method 48

1-Amino-1-methylcyclopropane

Bromine (2.87 ml, 0.056 mol) was added to a solution of sodium hydroxide (13.5 g, 0.338 mol) in water (100 ml) at 0–5° C. A slurry of 1-(1-methylcyclopropane)carboxamide (5.70 g 0.056 mol) in water (50 ml) was then added and reaction mixture stirred at 5° C. for 2 hours, then left to stand at ambient temperature for 24 hours. The mixture was then heated at 80° C. for 2.5 hours, allowed to cool and mixture distilled to give the title compound (bp 75–80° C.). NMR: 0.2 (q, 2H), 0.14 (q, 2H), 0.96 (s, 3H), 1.42 (s, 2H).

Method 49

1,3-Dimethoxy-2-methanesulphonyloxypropane

Triethylamine (5 ml, 0.036 mol) followed by slow addition of methanesulphonyl chloride (2.72 ml, 0.035 mol) was added to a solution of 1,3-dimethoxy-2-hydroxypropane (3.84 g, 0.032 mol) in dichloromethane (70 ml) cooled at 5° C. The mixture was then stirred at ambient temperature for 24 hours. The mixture was then absorbed onto silica gel and purified by chromatography eluting with dichloromethane/isohexane (1:1) to give the title compound (3.74 g, 59%). NMR: 3.15 (s, 3H), 3.28 (s, 6H), 3.52 (d, 4H), 4.78 (q, 1H).

Methods 50–52

The following compounds were prepared by a method analogous to that described in Method 49.

| Meth | Compound | NMR |
| --- | --- | --- |
| 50 | 1-Ethoxy-2-methanesulphonyloxypropane | 1.10 (t, 3H), 1.28 (d, 3H), 3.14 (s, 3H), 3.42–3.48 (m, 2H), 3.62–3.68 (m, 2H), 4.78 (q, 1H) |
| 51 | 1-Propoxy-2-methanesulphonyloxypropane | 0.86 (t, 3H), 1.28 (d, 3H), 1.51 (q, 2H), 3.33–3.40 (m, 2H), 3.44 (d, 2H), 3.69 (d, 3H), 4.78 (q, 1H) |
| 52 | 1,3-Diethoxy-2-methanesulphonyloxypropane | 1.12 (t, 6H), 3.16 (s, 3H), 3.41–3.45 (m, 4H), 3.55 (d, 4H), 4.75 (q, 1H) |

Method 53

1,3-Dimethoxy-2-azidopropane 1,3-Dimethoxy-2-methanesulphonyloxypropane (Method 49; 3.74 g, 19 mmol) and sodium azide (2.03 g, 31 mmol) in DMA (55 ml) was heated at 100° C. for 8 hours then left to stand at ambient temperature for 24 hours. The mixture was diluted with water, extracted with ethyl acetate, the extracts combined and washed with water, dried (MgSO$_4$) and the volatiles removed by evaporation to give the title compound (2.0 g, 74%) as a clear oil.

Methods 54–56

The following compounds were prepared by a method analogous to that described in Method 53.

| Meth | Compound | SM |
| --- | --- | --- |
| 54 | 1-Ethoxy-2-azidopropane | Method 50 |
| 55 | 1-Propoxy-2-azidopropane | Method 51 |
| 56 | 1,3-Diethoxy-2-azidopropane | Method 52 |

Method 57

1,3-Dimethoxy-2-aminopropane

10% Palladium on charcoal (500 mg) was added to a solution of 1,3-dimethoxy-2-azidopropane (Method 53; 2 g, 0.014 mol) in ethanol (40 ml) and the mixture stirred under an atmosphere of hydrogen at ambient temperature for 6 hours. The catalyst was removed by filtration through diatomaceous earth and the filter pad washed with ethanol to give a solution of the title compound in ethanol (20 ml).

Methods 58–60

The following compounds were prepared by a method analogous to that described in Method 57.

| Meth | Compound | SM |
|---|---|---|
| 58 | 1-Ethoxy-2-aminopropane | Method 54 |
| 59 | 1-Propoxy-2-aminopropane | Method 55 |
| 60 | 1,3-Diethoxy-2-aminopropane | Method 56 |

Example 67

The following illustrate representative pharmaceutical dosage forms containing the compound of formula (I), or a pharmaceutically acceptable salt or in vivo hydrolysable ester thereof (hereafter compound X), for therapeutic or prophylactic use in humans:-

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

| (e): Injection I | (50 mg/ml) |
|---|---|
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1 M Sodium hydroxide solution | 15.0% w/v |
| Water for injection | to 100% |

| (g): Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of formula (I):

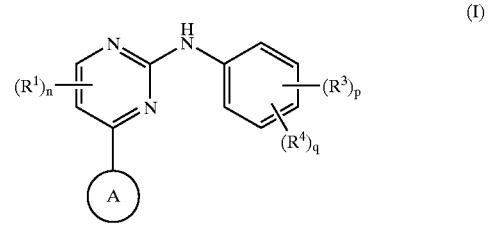

(I)

wherein:

Ring A is a group of formula (IA) or (IB):

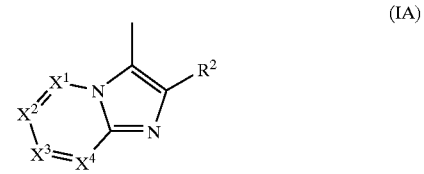

(IA)

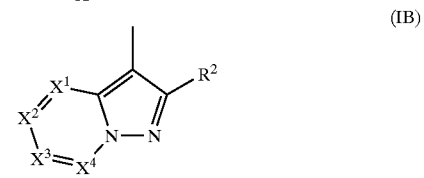

(IB)

wherein one or more of $X^1$, $X^2$, $X^3$ and $X^4$ are nitrogen and the others are $CR^5$ wherein the values of $R^5$ may be the same or different;

$R^1$ is halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkyl, $C_{1-6}$alkoxy, $C_{1-6}$alkanoyl, $N$-($C_{1-6}$alkyl)amino, $N,N$-($C_{1-6}$alkyl)$_2$amino, $C_{1-6}$alkanoylamino, $N$-($C_{1-6}$alkyl)carbamoyl, $N,N$-($C_{1-6}$alkyl)$_2$carbamoyl, $C_{1-6}$alkylS(O)$_a$ wherein a is 0 to 2, $N$-($C_{1-6}$alkyl)sulphamoyl or $N,N$-($C_{1-6}$alkyl)$_2$sulphamoyl; wherein $R^1$ may be optionally substituted on carbon by one or more $R^6$;

$R^2$ and $R^5$ are independently of one other selected from hydrogen, halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-4}$alkyl)carbamoyl, N,N-($C_{1-6}$ alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, phenyl, heterocyclic group, phenylthio or (heterocyclic group)thio; wherein any $R^2$ or $R^5$ may be optionally substituted on carbon by one or more $R^7$; and wherein if said heterocyclic group contains an —NH— moiety that nitrogen may be optionally substituted by a group selected from $R^8$;

n is 0 to 2, wherein the values of $R^1$ may be the same or different;

$R^3$ is halo, nitro, cyano, hydroxy, amino, carboxy, carbamoyl, mercapto, sulphamoyl, $C_{2-6}$alkenyl or $C_{2-6}$alkynyl;

p is 0–4; wherein the values of $R^3$ may be the same or different;

$R^4$ is a group A-E-; wherein

A is selected from $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$alkyl; wherein A may be optionally substituted on carbon by one or more $R^9$; and wherein if said heterocyclic group contains an —NH— moiety that nitrogen may be optionally substituted by a group selected from $R^{10}$;

E is a direct bond or —O—, —C(O)—, —OC(O)—, —C(O)O—, —N($R^a$)C(O)—, —C(O)N($R^a$)—, —N($R^a$)—, —S(O)$_a$—, —SO$_2$N($R^a$)— or —N($R^a$)SO$_2$—; wherein $R^a$ is hydrogen or $C_{1-6}$alkyl optionally substituted by one or more $R^{11}$ and a is 0–2;

$R^9$ is independently selected from oxo, halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$ alkyl)$_2$ amino, $C_{1-6}$alkanoylamino, N-($C_{1-6}$alkyl) carbamoyl, N,N-($C_{1-6}$alkyl)$_2$carbamoyl, $C_{1-6}$alkylS (O)$_a$ wherein a is 0 to 2, $C_{1-6}$alkoxycarbonyl, $C_{1-6}$alkoxycarbonylamino, benzyloxycarbonylamino, N-($C_{1-6}$alkyl)sulphamoyl and N,N-($C_{1-6}$alkyl)$_2$ sulphamoyl; wherein $R^9$ may be optionally substituted on carbon by one or more $R^{12}$;

q is 0–2; wherein the values of $R^4$ maybe the same or different; and wherein p+q$\leq$5;

$R^6$, $R^7$, $R^{11}$ and $R^{12}$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^8$ and $R^{10}$ are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl) carbamoyl, benzyl,benzyloxycarbonyl, benzoyl and phenylsulphonyl;

or a pharmaceutically acceptable salt or an in vivo hydrolysable ester thereof.

2. A compound of formula (I) as claimed in claim 1 wherein Ring A is a group of formula (IA) or a pharmaceutically acceptable salt or an in vivo hydrolysable ester thereof.

3. A compound of formula (I) as claimed in claim 1 wherein one of $X^1$, $X^2$, $X^3$ and $X^4$ are nitrogen and the others are $CR^5$ wherein the values of $R^5$ may be the same or different or a pharmaceutically acceptable salt or an in vivo hydrolysable ester thereof.

4. A compound of formula (I) as claimed in claim 1 wherein n is 0 or a pharmaceutically acceptable salt or an in vivo hydrolysable ester thereof.

5. A compound of formula (I) as claimed in claim 1 wherein $R^2$ is selected from hydrogen, $C_{1-6}$alkyl or N,N-($C_{1-6}$alkyl)$_2$amino or a pharmaceutically acceptable salt or an in vivo hydrolysable ester thereof.

6. A compound of formula (I) as claimed in any one of claim 1 wherein $R^5$ is selected from hydrogen, $C_{1-6}$alkyl or $C_{1-6}$alkoxy; wherein $R^5$ may be optionally substituted on carbon by one or more $R^7$; wherein $R^7$ is selected from halo or a pharmaceutically acceptable salt or an in vivo hydrolysable ester thereof.

7. A compound of formula (I) as claimed in claim 1 wherein $R^3$ is sulphamoyl or halo or a pharmaceutically acceptable salt or an in vivo hydrolysable ester thereof.

8. A compound of formula (I) as claimed in claim 1 wherein p is 0 or 1 or a pharmaceutically acceptable salt or an in vivo hydrolysable ester thereof.

9. A compound of formula (I) as claimed in claim 1 wherein $R^4$ is a group A-E-; wherein:

A is selected from $C_{1-6}$alkyl, $C_{3-8}$cycloalkyl, (heterocyclic group)$C_{1-6}$alkyl or $C_{3-8}$cycloalkyl$C_{1-6}$alkyl; wherein A may be optionally substituted on carbon by one or more $R^9$;

E is —N($R^a$)SO$_2$—; wherein $R^a$ is hydrogen or $C_{1-6}$alkyl;

$R^9$ is independently selected from hydroxy, $C_{1-6}$alkyl, $C_{2-6}$alkenyl, $C_{2-6}$alkynyl, $C_{1-6}$alkoxy, N,N-($C_{1-6}$alkyl)$_2$ amino or $C_{1-6}$alkylS(O)$_a$ wherein a is 0;

or a pharmaceutically acceptable salt or an in vivo hydrolysable ester thereof.

10. A compound of formula (I) as claimed in claim 1 wherein q is 0 or 1 or a pharmaceutically acceptable salt or an in vivo hydrolysable ester thereof.

11. A compound of formula (I) as claimed in claim 1 wherein p+q is 0, 1 or 2; wherein the values of $R^3$ may be the same or different and the values of $R^4$ may be the same or different; or a pharmaceutically acceptable salt or an in vivo hydrolysable ester thereof.

12. A compound of formula (I)

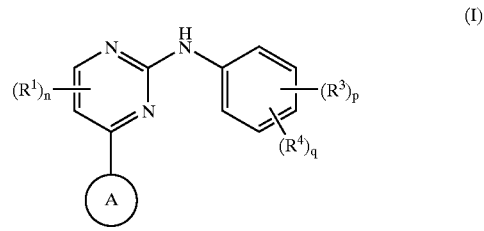

wherein:

Ring A is a group of formula (IA):

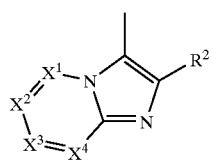
(IA)

wherein one of $X^1$, $X^2$, $X^3$ and $X^4$ is nitrogen and the others are $CR^5$; wherein the values of $R^5$ may be the same or different;

n is 0;

$R^2$ is selected from hydrogen, methyl, ethyl or N,N-dimethylamino;

$R^5$ is selected from hydrogen, methyl, methoxy or 2,2,2-trifluoroethoxy;

$R^3$ is sulphamoyl or fluoro;

p is 0 or 1;

$R^4$ is N-methylsulphamoyl, N-cyclopropylmethylsulphamoyl, N-ethylsulphamoyl, N-propylsulphamoyl, N-allylsulphamoyl, N-2-propynylsulphamoyl, N-cyclobutylsulphamoyl, N-t-butylsulphamoyl, N-cyclopropylsulphamoyl, N-(2-dimethylaminoethyl)sulphamoyl, N-(2-methoxyethyl)sulphamoyl, N-(2-pyrazol-1-ylethyl)sulphamoyl, N-methyl-N-(2-methoxyethyl)sulphamoyl, N-(1-cyclopropylethyl)sulphamoyl, N-(3-dimethylaminopropyl)sulphamoyl, N-(3-methoxypropyl)sulphamoyl, N-(3-hydroxy-2-hydroxymethylprop-2-yl)sulphamoyl, N-(1,3-dihydroxyprop-2-yl)sulphamoyl, N-(3-morpholino-2-methylprop-2-yl)sulphamoyl, N-(1,3-dimethoxyprop-2-yl)sulphamoyl, N-(1,3-diethoxyprop-2-yl)sulphamoyl, N-(1-methoxyprop-2-yl)sulphamoyl, N-(1-ethoxyprop-2-yl)sulphamoyl, N-(1-hydroxyprop-2-yl)sulphamoyl, N-(3-methylthio-2-methylprop-2-yl)sulphamoyl, N-(3-pyrrolidin-1-yl-2-methylprop-2-yl)sulphamoyl, N-(3-methoxy-2-methylprop-2-yl)sulphamoyl, N-(2-methoxy-2-methylpropyl)sulphamoyl, N-(1-propoxyprop-2-yl)sulphamoyl or N-(3-hydroxy-2-methylprop-2-yl)sulphamoyl;

q is 0 or 1;

p+q is 0, 1 or 2; wherein the values of $R^3$ may be the same or different and the values of $R^4$ may be the same or different;

or a pharmaceutically acceptable salt or an in vivo hydrolysable ester thereof.

13. A compound of formula (I):

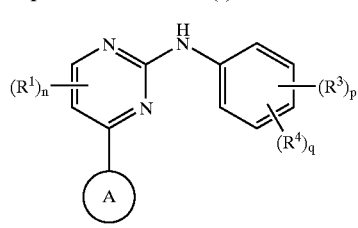
(I)

selected from:

2-{4-[N-(2-Methoxyethyl)sulphamoyl]anilino}-4-(imidazo[1,2b]pyridazin-3-yl)pyrimidine;

2-{4-[N-(3-Methoxypropyl)sulphamoyl]anilino}-4-(imidazo[1,2b]pyridazin-3-yl)pyrimidine;

2-[4-(N-Propylsulphamoyl)anilino]-4-(imidazo[1,2b]pyridazin-3-yl)pyrimidine;

2-{4-[N-(2-Methoxyethyl)sulphamoyl]anilino}-4-(2-methylimidazo[1,2b]pyridazin-3-yl)pyrimidine;

2-[4-(N-Methylsulphamoyl)anilino]-4-(2-methylimidazo[1,2b]pyridazin-3-yl)pyrimidine;

2-{4-[N-(2-(1-Pyrazolyl)ethyl)sulphamoyl]anilino}-4-(imidazo[1,2b]pyridazin-3-yl)pyrimidine;

2-{4-[N-(1,3-Diethoxyprop-2-yl)sulphamoyl]anilino}-4-(imidazo[1,2b]pyridazin-3-yl)pyrimidine;

2-{4-[N-(1,3-Dimethoxyprop-2-yl)sulphamoyl]anilino}-4-(imidazo[1,2b]pyridazin-3-yl)pyrimidine;

2-{4-[N-(1-Ethoxyprop-2-yl)sulphamoyl]anilino}-4-(imidazo[1,2b]pyridazin-3-yl)pyrimidine;

2-{4-[N-(2-Ethoxyethyl)sulphamoyl]anilino}-4-(imidazo[1,2b]pyridazin-3-yl)pyrimidine;

or a pharmaceutically acceptable salt or an in vivo hydrolysable ester thereof.

14. A process for preparing a compound of formula (I) as claimed in claim 1 or a pharmaceutically acceptable salt or an in vivo hydrolysable ester thereof which process (wherein variable groups are, unless otherwise specified, as defined in claim 1) comprises of:

a) reaction of a pyrmidine of formula (II):

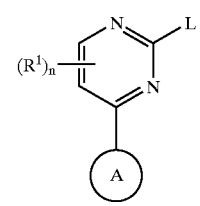
(II)

wherein L is a displaceable group; with an amine of formula (III):

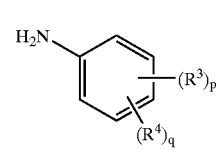
(III)

b) reacting a pyrimidine of formula (IV):

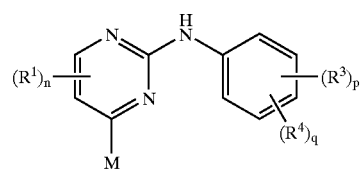
(IV)

with a compound of the formula (V):

(V)

wherein one of M and Q is a displaceable group X and the other is an metallic reagent Y; or c) reacting a compounds of formula (VI):

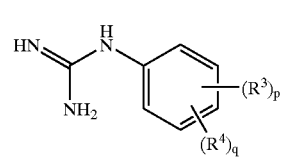
(VI)

with a compound of formula (VII):

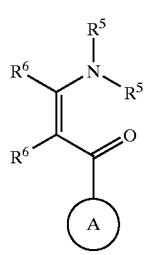
(VII)

wherein $R^5$ is $C_{1-6}$alkyl and $R^6$ is hydrogen or $R^1$;

d) reacting an amino compound of formula (VIII):

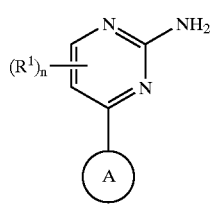
(VIII)

with a compound of formula (IX):

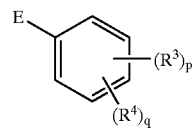

wherein E is a displaceable group; and thereafter if necessary:

i) converting a compound of the formula (I) into another compound of the formula (I);
ii) removing any protecting groups;
iii) forming a pharmaceutically acceptable salt or in vivo hydrolysable ester.

15. A pharmaceutical composition which comprises a compound of the formula (I), or a pharmaceutically acceptable salt or in vivo hydrolysable ester thereof, as claimed in any one of claims 1–13 in association with a pharmaceutically-acceptable diluent or carrier.

16. A method for inhibiting cyclin-dependent kinase CDK2, CDK4 or CDK6 in a warm-blooded animal, which comprises administering to said animal an inhibitory amount of a compound of formula (I) or a pharmaceutically acceptable salt or in vivo hydrolysable ester thereof as claimed in any one of claims 1–13.

* * * * *